United States Patent
Zeng et al.

(10) Patent No.: US 9,963,516 B2
(45) Date of Patent: *May 8, 2018

(54) STABLE COMPOSITIONS OF HIGH-CONCENTRATION ALLOTYPE-SELECTED ANTIBODIES FOR SMALL-VOLUME ADMINISTRATION

(71) Applicant: Immunomedics, Inc., Morris Plains, NJ (US)

(72) Inventors: Li Zeng, Edison, NJ (US); Rohini Mitra, Brigdewater, NJ (US); Edmund A. Rossi, Woodland Park, NJ (US); Hans J. Hansen, Picayune, MS (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/592,871

(22) Filed: May 11, 2017

(65) Prior Publication Data

US 2017/0260287 A1 Sep. 14, 2017

Related U.S. Application Data

(60) Division of application No. 14/876,200, filed on Oct. 6, 2015, now Pat. No. 9,683,050, which is a continuation of application No. 14/163,443, filed on Jan. 24, 2014, now Pat. No. 9,180,205, which is a division of application No. 14/132,549, filed on Dec. 18, 2013, now Pat. No. 9,468,689, which is a division of application No. 13/461,307, filed on May 1, 2012, now Pat. No. 8,658,773.

(60) Provisional application No. 61/481,489, filed on May 2, 2011, provisional application No. 61/509,850, filed on Jul. 20, 2011.

(51) Int. Cl.

| | |
|---|---|
| *C07K 16/30* | (2006.01) |
| *C07K 16/28* | (2006.01) |
| *A61K 51/08* | (2006.01) |
| *A61K 51/10* | (2006.01) |
| *A61K 39/00* | (2006.01) |

(52) U.S. Cl.
CPC ........ *C07K 16/3092* (2013.01); *A61K 51/088* (2013.01); *A61K 51/1027* (2013.01); *A61K 51/1045* (2013.01); *C07K 16/2803* (2013.01); *C07K 16/2833* (2013.01); *C07K 16/2887* (2013.01); *C07K 16/30* (2013.01); *C07K 16/3007* (2013.01); *A61K 2039/505* (2013.01); *A61K 2039/54* (2013.01); *A61K 2039/545* (2013.01); *A61K 2039/55505* (2013.01); *A61K 2039/55511* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 5,429,746 A | 7/1995 | Shadle et al. | |
| 5,789,554 A | 8/1998 | Leung et al. | |
| 5,876,961 A | 3/1999 | Crowe et al. | |
| 6,171,586 B1 | 1/2001 | Lam et al. | |
| 6,187,287 B1 | 2/2001 | Leung et al. | |
| 6,252,055 B1 | 6/2001 | Relton | |
| 6,676,924 B2 | 1/2004 | Hansen et al. | |
| 6,870,034 B2 | 3/2005 | Breece et al. | |
| 6,893,639 B2 | 5/2005 | Levy et al. | |
| 6,991,790 B1 | 1/2006 | Lam et al. | |
| 7,038,017 B2 | 5/2006 | Rinderknecht et al. | |
| 7,074,403 B1 | 7/2006 | Goldenberg et al. | |
| 7,109,304 B2 | 9/2006 | Hansen et al. | |
| 7,138,496 B2 | 11/2006 | Hua et al. | |

(Continued)

FOREIGN PATENT DOCUMENTS

| | | |
|---|---|---|
| WO | 9505468 | 2/1995 |
| WO | 2007103469 | 9/2007 |

(Continued)

OTHER PUBLICATIONS

Abbott: Humira, US, Jan. 31, 2003, p. 1-13, Retrieved from the Internet: URL:http://www.fda.gov/ohrms/dockets/ac/03 /briefing/ 3930B1_02_B-Abbott-Humira Prescribing Info.pdf [retrieved on Mar. 20, 2014].

(Continued)

*Primary Examiner* — Yunsoo Kim

(74) *Attorney, Agent, or Firm* — Richard A. Nakashima

(57) ABSTRACT

Disclosed are methods, compositions and uses of high concentration antibody or immunoglobulin formulations for subcutaneous, intramuscular, transdermal or other local (regional) administration, in a volume of than 3, less than 2 or less than 1 ml. Preferably, the formulation contains a high concentration formulation (HCF) buffer comprising phosphate, citrate, polysorbate 80 and mannitol at a pH of about 5.2. The formulation more preferably comprises at least 100, 150, 200, 250 mg/ml or 300 mg/ml of antibody. The methods for preparing the high concentration formulation include ultrafiltration and diafiltration to concentrate the antibody and exchange the medium for HCF buffer. Other embodiments concern use of non-G1m1 (nG1m1) allotype antibodies, such as G1m3 and/or a nG1m1,2 antibodies. The nG1m1 antibodies show decreased immunogenicity compared to G1m1 antibodies.

31 Claims, 8 Drawing Sheets

(56) References Cited

U.S. PATENT DOCUMENTS

| | | | |
|---|---|---|---|
| 7,151,164 B2 | 12/2006 | Hansen et al. | |
| 7,238,785 B2 | 7/2007 | Govindan et al. | |
| 7,251,164 B2 | 7/2007 | Okhonin et al. | |
| 7,282,567 B2 | 10/2007 | Goldenberg et al. | |
| 7,300,655 B2 | 11/2007 | Hansen et al. | |
| 7,312,318 B2 | 12/2007 | Hansen et al. | |
| 7,385,040 B2 | 6/2008 | Johansson et al. | |
| 7,387,773 B2 | 6/2008 | Murray et al. | |
| 7,435,803 B2 | 10/2008 | Hansen et al. | |
| 7,521,056 B2 | 4/2009 | Chang et al. | |
| 7,527,787 B2 | 5/2009 | Chang et al. | |
| 7,534,866 B2 | 5/2009 | Chang et al. | |
| 7,541,440 B2 | 6/2009 | Goldenberg et al. | |
| 7,550,143 B2 | 6/2009 | Chang et al. | |
| 7,592,004 B2 | 9/2009 | Kaisheva et al. | |
| 7,612,180 B2 | 11/2009 | Goldenberg et al. | |
| 7,625,560 B2 | 12/2009 | Basi et al. | |
| 7,635,473 B2 | 12/2009 | Warne et al. | |
| 7,666,400 B2 | 2/2010 | Chang et al. | |
| 7,772,373 B2 | 8/2010 | Hansen et al. | |
| 7,829,525 B2 | 11/2010 | Frevert | |
| 7,847,071 B2 | 12/2010 | Bonnerjea et al. | |
| 7,858,070 B2 | 12/2010 | Chang et al. | |
| 7,863,426 B2 | 1/2011 | Wan et al. | |
| 7,871,622 B2 | 1/2011 | Chang et al. | |
| 7,901,680 B2 | 3/2011 | Chang et al. | |
| 7,906,118 B2 | 3/2011 | Chang et al. | |
| 7,906,121 B2 | 3/2011 | Chang et al. | |
| 7,919,087 B2 | 4/2011 | Hansen et al. | |
| 7,931,903 B2 | 4/2011 | Hansen et al. | |
| 8,658,773 B2* | 2/2014 | Zeng | A61K 39/39591 530/412 |
| 9,180,205 B2 | 11/2015 | Zeng et al. | |
| 9,468,689 B2* | 10/2016 | Zeng | A61K 47/48369 |
| 2001/0014326 A1 | 8/2001 | Andya et al. | |
| 2003/0004094 A1 | 1/2003 | Ghose et al. | |
| 2004/0033228 A1 | 2/2004 | Krause et al. | |
| 2004/0033561 A1 | 2/2004 | O'Keefe et al. | |
| 2004/0208870 A1 | 10/2004 | Allan | |
| 2005/0053666 A1 | 3/2005 | Tzannis et al. | |
| 2005/0118167 A1 | 6/2005 | Okada et al. | |
| 2006/0152846 A1 | 7/2006 | Krause et al. | |
| 2006/0193850 A1 | 8/2006 | Warne et al. | |
| 2007/0031402 A1 | 2/2007 | Zhang et al. | |
| 2007/0184050 A1 | 8/2007 | Ishikawa et al. | |
| 2007/0258981 A1 | 11/2007 | Hilbert et al. | |
| 2008/0064856 A1 | 3/2008 | Warne et al. | |
| 2008/0152658 A1 | 6/2008 | Dagan et al. | |
| 2008/0306247 A1 | 12/2008 | Mizushima et al. | |
| 2009/0068196 A1 | 3/2009 | Goldbach et al. | |
| 2009/0104184 A1 | 4/2009 | Flemming et al. | |
| 2009/0117111 A1 | 5/2009 | Aukerman et al. | |
| 2009/0239259 A1 | 9/2009 | Hsieh | |
| 2009/0269302 A1 | 10/2009 | Salfeld et al. | |
| 2009/0291062 A1 | 11/2009 | Fraunhofer et al. | |
| 2010/0034738 A1 | 2/2010 | Goldenberg et al. | |
| 2010/0074885 A1 | 3/2010 | Schiff et al. | |
| 2010/0158899 A1 | 6/2010 | Andya et al. | |
| 2010/0172862 A1 | 7/2010 | Correia et al. | |
| 2010/0189721 A1 | 7/2010 | Brisbane et al. | |
| 2010/0209434 A1 | 8/2010 | Bishop et al. | |
| 2010/0221187 A1 | 9/2010 | Lieburg et al. | |
| 2010/0226884 A1 | 9/2010 | Chang et al. | |
| 2010/0260766 A1 | 10/2010 | Srivastava et al. | |
| 2010/0278822 A1 | 11/2010 | Fraunhofer et al. | |
| 2010/0303827 A1 | 12/2010 | Sharma et al. | |
| 2011/0020328 A1 | 1/2011 | Brisbane et al. | |
| 2011/0070225 A1 | 3/2011 | Goldbach et al. | |
| 2011/0071054 A1 | 3/2011 | Simard | |
| 2011/0071276 A1 | 3/2011 | Simard | |
| 2011/0300066 A1 | 12/2011 | Chang et al. | |
| 2011/0305631 A1 | 12/2011 | Govindan et al. | |

FOREIGN PATENT DOCUMENTS

| | | |
|---|---|---|
| WO | 2008028946 | 3/2008 |
| WO | 2008137915 | 11/2008 |
| WO | 2009006301 | 1/2009 |
| WO | 2009138484 | 11/2009 |
| WO | 2010011697 | 1/2010 |

OTHER PUBLICATIONS

Carmichael et al., "Peptide-mediated transdermal delivery of botulinum neurotoxin type A reduces neurogenic inflammation in the skin", Pain. May 2010;149(2):316-24. Epub Mar. 23, 2010.

Chen et al., "Transdermal protein delivery by a coadministered peptide identified via phage display", Nat Biotechnol. Apr. 2006;24(4):455-60.

Ellebrecht et al., "Subcutaneous veltuzumab, a humanized anti-CD20 antibody, in the treatment of refractory pemphigus vulgaris", JAMA Dermatol. Dec. 2014;150(12):1331-5.

Goldenberg et al., "Properties and structure-function relationships of veltuzumab (hA20), a humanized anti-CD20 monoclonal antibody", Blood. Jan. 29, 2009;113(5):1062-70.

Golovanov et al., "A simple method for improving protein solubility and long-term stability", J Am Chem Soc. Jul. 28, 2004;126(29):8933-9.

Haddad et al., "Home therapy with subcutaneous immunoglobulins for patients with primary immunodeficiency diseases", Transfus Apher Sci. Jun. 2012;46(3):315-21.

Jefferis et al., "Human immunoglobulin allotypes: possible implications for immunogenicity", MAbs. Jul.-Aug. 2009;1(4):1-7.

Jurynczyk et al., "Immune regulation of multiple sclerosis by transdermally applied myelin peptides", Ann Neurol. Nov. 2010;68(5):593-601.

Kavanaugh et al., "Golimumab, a new human tumor necrosis factor alpha antibody, administered every four weeks as a subcutaneous injection in psoriatic arthritis: Twenty-four-week efficacy and safety results of a randomized, placebo-controlled study", Arthritis Rheum. Apr. 2009;60(4):976-86.

Kheddo et al., "The effect of arginine glutamate on the stability of monoclonal antibodies in solution", Int J Pharm. Oct. 1, 2014;473(1-2):126-33.

Kim et al., "Biochemical enhancement of transdermal delivery with magainin peptide: modification of electrostatic interactions by changing pH", Int J Pharm. Oct. 1, 2008;362(1-2):20-8.

Liebman et al., "Low-dose anti-CD20 veltuzumab given intravenously or subcutaneously is active in relapsed immune thrombocytopenia: a phase I study", Br J Haematol. Sep. 2013;162(5):693-701.

Lundin et al., "Phase II trial of subcutaneous anti-CD52 monoclonal antibody alemtuzumab (Campath-1H) as first-line treatment for patients with B-cell chronic lymphocytic leukemia (B-CLL)", Blood. Aug. 1, 2002;100(3):768-73.

Magdelaine-Beuzelin et al., "IgG1 heavy chain-coding gene polymorphism (G1m allotypes) and development of antibodies-to-infliximab", Pharmacogenet Genomics. May 2009;19(5):383-7.

Morchhauser et al., "Humanized anti-CD20 antibody, veltuzumab, in refractory/recurrent non-Hodgkin's lymphoma: phase I/II results", J Clin Oncol. Jul. 10, 2009;27(20):3346-53.

Namboodiri et al., "Differential inhibition of trastuzumab- and cetuximab-induced cytotoxicity of cancer cells by immunoglobulin G1 expressing different GM allotypes", Clin Exp Immunol. Dec. 2011;166(3):361-5.

Negrea et al., "Subcutaneous injections of low-dose veltuzumab (humanized anti-CD20 antibody) are safe and active in patients with indolent non-Hodgkin's lymphoma", Haematologica. Apr. 2011;96(4):567-73.

Robak et al., "New anti-CD20 monoclonal antibodies for the treatment of B-cell lymphoid malignancies", BioDrugs. Feb. 1, 2011;25(1):13-25.

Stickler et al., "The human G1m1 allotype associates with CD4+ T-cell responsiveness to a highly conserved IgG1 aonstant region

(56) References Cited

OTHER PUBLICATIONS peptide and confers an asparaginyl endopeptidase cleavage site", Genes Immun. Apr. 2011;12 (3):213-21.

Uchida et al., "Development of an efficient transdermal delivery system of small interfering RNA using functional peptides, Tat and AT-1002", Chem Pharm Bull (Tokyo). Feb. 2011;59(2):196-201.

Wang et al., "Arginine-rich intracellular delivery peptides noncovalently transport protein into living cells", Biochem Biophys Res Commun. Aug. 4, 2006;346(3):758-67.

Warne et al., "Development of high concentration protein biopharmaceuticals: the use of platform approaches in formulation development", Eur J Pharm Biopharm. Jun. 2011;78(2):208-12.

\* cited by examiner (B) Reducing gel
(A) Non reducing gel

FIG. 7

```
V-mab  ASTKGPSVFPLAPSSKSTSGGTAALGCLVKDYFPEPVTVSWNSGALTSGV
R-mab  **************************************************

V-mab  HTFPAVLQSSGLYSLSSVVTVPSSSLGTQTYICNVNHKPSNTKVDKRVEP
R-mab  ********************************************KA**

V-mab  KSCDKTHTCPPCPAPELLGGPSVFLFPPKPKDTLMISRTPEVTCVVVDVS
R-mab  **************************************************

V-mab  HEDPEVKFNWYVDGVEVHNAKTKPREEQYNSTYRVVSVLTVLHQDWLNGK
R-mab  **************************************************

V-mab  EYKCKVSNKALPAPIEKTISKAKGQPREPQVYTLPPSREEMTKNQVSLTC
R-mab  ********************************SR*D*L***********

V-mab  LVKGFYPSDIAVEWES

FIG. 8 hL243-g4p heavy chain

QVQLQQSGSELKKPGASVKVSCKASGFTFTNYGMNWVKQAPGQGLKWMGWIN
TYTREPTYADDFKGRFAFSLDTSVSTAYLQISSLKADDTAVYFCARDITAVVPTG
FDYWGQGSLVTVSSASTKGPSVFPLAPCSRSTSESTAALGCLVKDYFPEPVTVSW
NSGALTSGVHTFPAVLQSSGLYSLSSVVTVPSSSLGTKTYTCNVDHKPSNTKVDK
RVESKYGPPCPPCPAPEFLGGPSVFLFPPKPKDTLMISRTPEVTCVVVDVSQEDPE
VQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALH
NHYTQKSLSLSLGK (SEQ ID NO:37)

hL243-g4p heavy chain constant region

ASTKGPSVFPLAPCSRSTSESTAALGCLVKDYFPEPVTVSWNSGALTSGVHTFPA
VLQSSGLYSLSSVVTVPSSSLGTKTYTCNVDHKPSNTKVDKRVESKYGPPCPPCP
APEFLGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSLG
K (SEQ ID NO:38)

hL243 light chain

DIQLTQSPSSLSASVGDRVTITCRASENIYSNLAWYRQKPGKAPKLLVFAASNLA
DGVPSRFSGSGSGTDYTFTISSLQPEDIATYYCQHFWTTPWAFGGGTKLQIKRTV
AAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC (SEQ
ID NO:39)

hL243 light chain constant region

TVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO:40)

… # STABLE COMPOSITIONS OF HIGH-CONCENTRATION ALLOTYPE-SELECTED ANTIBODIES FOR SMALL-VOLUME ADMINISTRATION

RELATED APPLICATIONS

This application is a divisional of U.S. patent application Ser. No. 14/876,200, filed Oct. 6, 2015, which was a continuation of U.S. patent application Ser. No. 14/163,443 (now U.S. Pat. No. 9,180,205), filed Jan. 24, 2014, which was a divisional of U.S. patent application Ser. No. 14/132,549 (now U.S. Pat. No. 9,468,689), filed Dec. 18, 2013, which was a divisional of U.S. patent application Ser. No. 13/461,307 (now U.S. Pat. No. 8,658,773), filed May 1, 2012, which claimed the benefit under 35 U.S.C. 119(e) of provisional U.S. Patent Application Ser. Nos. 61/481,489, filed May 2, 2011, and 61/509,850, filed Jul. 20, 2011.

SEQUENCE LISTING

The instant application contains a Sequence Listing which has been submitted in ASCII format via EFS-Web and is hereby incorporated by reference in its entirety. Said ASCII copy, created on Apr. 27, 2012, is named IMM332US.txt and is 26,473 bytes in size.

FIELD OF THE INVENTION

The present invention concerns compositions and methods of production and use of stable, highly concentrated formulations of immunoglobulins, antibodies and/or antigen-binding antibody fragments. In preferred embodiments, the immunoglobulins, antibodies or fragments thereof may be non-specific human immunoglobulin (e.g., IVIg), antibodies that bind to antigens such as CD22 (e.g., epratuzumab), CD20 (e.g., veltuzumab; GA101), CD74 (e.g., milatuzumab) or HLA-DR (e.g., IMMU-114 or hL243), although antibodies against other antigenic targets may be utilized. In more preferred embodiments, the allotypes of the antibodies or fragments thereof are selected to be non-G1m1 human allotypes, such as G1m3. Even more preferred is the nG1m1,2 null allotype. The antibodies or fragments thereof may be either naked (unconjugated) or may be conjugated to at least one therapeutic or diagnostic agent that is not a cytotoxic agent or a radionuclide. The concentrated antibody formulations are of use for the treatment of a variety of diseases, such as autoimmune disease, immune dysregulation disease, infectious disease, cancer (e.g., carcinoma, sarcoma, melanoma, glioma, neuroblastoma, lymphoma, leukemia, chronic lymphocytic leukemia, follicular lymphoma, diffused large B-cell lymphoma, T-cell lymphoma or leukemia, multiple myeloma or non-Hodgkin's lymphoma), cardiovascular, neurological or metabolic disease. In other preferred embodiments, the concentrated antibody formulations may be administered by subcutaneous, intramuscular or transdermal administration, although other modes of administration (e.g., intrathecal, intraperitoneal, intraocular, intracranial, etc.) are contemplated. In most preferred embodiments, the antibodies or fragments thereof are concentrated to at least 80 mg/ml, more preferably at least 100 mg/ml, more preferably at least 125 mg/ml, more preferably at least 150 mg/ml, more preferably at least 175 mg/ml, more preferably at least 200 mg/ml, more preferably at least 225 mg/ml, more preferably at least 250 mg/ml, more preferably at least 300 mg/ml in a slightly acidic aqueous buffer solution. Other components of the formulation may include buffers, such as citrate or phosphate, salts such as sodium chloride, surfactants such as polysorbate 80 and/or polyols such as mannitol.

BACKGROUND

Administration of monoclonal antibodies or fragments thereof has been proposed for diagnosis and/or therapy of a wide variety of disease states, such as cancer, infectious diseases, autoimmune or immune dysfunction disease, neurological diseases, cardiovascular disease and metabolic disease. (See, e.g., Nadler et al., 1980, Cancer Res 40:3147-54; Ritz and Schlossman, 1982, Blood 59:1-11; Waldmann, 2003, Nature Med 9:269-77; Ibbotson et al., 2003, Am J Cardiovasc Drugs 3:381-86; Dorner et al., 2009, Nat Rev Rheumatol 5:433-41; Pul et al., 2011, Expert Opin Biol Ther 11:343-57). Human immunoglobulin mixtures are also used, particularly by subcutaneous injection, for the treatment of hepatitis, as well as various autoimmune diseases by intravenous infusion (see, e.g., Powell et al., 2006, Clin Transplant 20:524-25; Stiehm, 1997, Pediatr Infect Dis J 16:696-707; Zandman et al., Clin Rev Allergy Immunol [Epub ahead of print, Jul. 6, 2011]; Kaveri et al., 2011, Clin Exp Immunol 164:2-5).

While intravenous infusion has been the standard mode of antibody administration, infusion-related reactions such as rash, urticaria, erythema, pruritus, hypotension, bronchospasm or anaphylaxis may be severe and can significantly limit the rate of antibody infusion. (See, e.g., Kang and Saif, 2007, J Supportive Oncol 5:451-57; Vogel, 2010, Clin J Oncol Nursing 14:E10-21). In part to address the incidence of infusion-related reactions, subcutaneous administration of therapeutic antibodies has been proposed (Lundin et al., 2002, Blood 100:768-73; Kavanaugh et al., Arthritis Rheum, 2009, 60:976-86; Negrea et al. 2011, Haematologica 96:567-73). Intramuscular administration is also given, such as with IVIg (Marzano et al., 2010, Minerva Med 101:373-83; Pauwelyn et al., 2010, Transplant Proc 42:4399-402; Filipponi et al., 2010, Dig Liver Dis 42:509-14). Another alternative is transdermal administration (e.g., Burton et al., 2011, Pharm Res 28:31-40; Wendorf et al., 2011, Pharm Res 28:22-30; Koutsonanos et al., 2009, PLoS One 4:e4773). While infusion-site reactions may still occur, subcutaneous, intramuscular or transdermal administration would result in decreased health care costs by avoiding the need for lengthy intravenous administration and dedicated infusion suites and staff, and may also decrease the incidence of systemic infusion reactions (Lundin et al., 2002, Blood 100:768-73; Wasserman, 2008, Patient Preference and Adherence, 2:163-66; Negrea et al. 2011, Haematologica 96:567-73), as well as being more tolerable and convenient for the patient, including the possibility for self-administration. Because of the lower injection volume associated with subcutaneous, intramuscular or transdermal administration, a need exists for more concentrated antibody or immunoglobulin formulations that are stable for long periods of time and can be administered subcutaneously, intramuscularly or transdermally (or by other routes requiring small volumes of injectate).

SUMMARY

The present invention concerns compositions and methods of production and use of stable, highly concentrated formulations of therapeutic immunoglobulins, monoclonal antibodies or antigen-binding fragments thereof and use for low-volume injections. Although many methods of antibody production are known in the art and may be utilized, preferably an expression vector(s) encoding the antibody or fragment is transfected into a mammalian cell line such as SpEEE, SpESF or SpESF-X (see, e.g., U.S. Pat. Nos. 7,531,327; 7,537,930; 7,608,425; and 7,785,880; the Examples section of each of which is incorporated herein by reference). More preferably, both transfection and antibody expression occur in serum-free medium to decrease the expense of production and remove a source of contaminating proteins. The antibody is produced into the cell culture medium for further purification.

In other preferred embodiments, the antibody may be purified from cell culture medium by sequential chromatography, for example by affinity and ion exchange column chromatography. Non-limiting examples include affinity chromatography on Protein A, anion-exchange chromatography on Q-SEPHAROSE® and cation-exchange chromatography on SP-SEPHAROSE®. More preferably, the antibody is bound to the SP-SEPHAROSE® resin in pH 5 citrate buffer and eluted from the column with pH 6 citrate buffer in 0.15 M NaCl. The eluate from the SP-SEPHAROSE® column may be filtered through, for example, a 20 nm filter for virus removal. The purified antibody may then be diafiltered, for example using an AMICON® Ultrafiltration Cell with a 50 KD MW cut-off filter to exchange the medium with a high concentration formulation buffer (HCF buffer) and to concentrate the antibody for storage. In most preferred embodiments, the HCF buffer solution may comprise phosphate buffer (pH 5.2), sodium chloride, Polysorbate 80, citrate and mannitol. Polysorbate 80 serves to decrease protein aggregation, while mannitol stabilizes the antibody in aqueous medium. The diafiltration concentrates the antibody to preferably at least 80 mg/ml, more preferably at least 100 mg/ml, more preferably at least 150 mg/ml, more preferably at least 200 mg/ml, more preferably at least 300 mg/ml final concentration. The concentrated antibody exhibits little or no aggregation and preferably is stable in liquid form at 2-8° for at least 10 months. In even more preferred embodiments, the Polysorbate 80 is added to the concentrated antibody after the ultrafiltration step.

The stable, highly concentrated antibody is of use for preparing medicaments for administration to subjects, preferably by subcutaneous, transdermal or intramuscular administration. However, the skilled artisan will realize that other forms of administration known in the art, such as intravenous, intraperitoneal, intraventricular, intraocular, and/or intrathecal administration may be utilized.

Antibodies of use may bind to any disease-associated antigen known in the art. Where the disease state is cancer, for example, many antigens expressed by or otherwise associated with tumor cells are known in the art, including but not limited to, carbonic anhydrase IX, alpha-fetoprotein, α-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CXCR4, CXCR7, CXCL12, HIF-1α, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUC13, MUC16, MUM-1/2, MUM-3, NCA66, NCA95, NCA90, pancreatic cancer mucin, placental growth factor, p53, PLAGL2, prostatic acid phosphatase, PSA, PRAME, PSMA, PlGF, ILGF, ILGF-1R, IL-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, TROP-2, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin Cancer Res 2006, 12:5023-32; Parmiani et al., J Immunol 2007, 178: 1975-79; Novellino et al. Cancer Immunol Immunother 2005, 54:187-207). Preferably, the antibody binds to CD74, CD20, CD22 or HLA-DR.

Exemplary antibodies that may be utilized include, but are not limited to, hR1 (anti-IGF-1R, U.S. patent application Ser. No. 12/722,645, filed Mar. 12, 2010), hPAM4 (anti-mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the Examples section of each cited patent or application incorporated herein by reference. More preferably, the antibody is hA20 (veltuzumab), hLL2 (epratuzumab), hLL1 (milatuzumab) or hL243 (IMMU-114).

Alternative antibodies of use include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab tiuxetan (anti-CD20), panitumumab (anti-EGFR), rituximab (anti-CD20), tositumomab (anti-CD20), trastuzumab (anti-ErbB2), abagovomab (anti-CA-125), adecatumumab (anti-EpCAM), atlizumab (anti-IL-6 receptor), benralizumab (anti-CD125), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), muromonab-CD3 (anti-CD3 receptor), natalizumab (anti-α4 integrin), omalizumab (anti-IgE); anti-TNF-α antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), Benlysta (Human Genome Sciences); antibodies for therapy of Alzheimer's disease such as Alz 50 (Ksiezak-Reding et al., 1987, J Biol Chem 263:7943-47), gantenerumab, solanezumab and infliximab; anti-fibrin antibodies like 59D8, T2G1s, MH1; anti-HIV antibodies such as P4/D10 (U.S. patent application Ser. No. 11/745,692), Ab 75, Ab 76, Ab 77 (Paulik et al., 1999, Biochem Pharmacol 58:1781-90); and antibodies against pathogens such as CR6261 (anti-influenza), exbivirumab (anti-hepatitis B), felvizumab (anti-respiratory syncytial virus), foravirumab (anti-rabies virus), motavizumab (anti-respiratory syncytial virus), palivizumab (anti-respiratory syncytial virus), panobacumab (anti-Pseudomonas), rafivirumab (anti-rabies virus), regavirumab (anti-cytomegalovirus), sevirumab (anti-cytomegalovirus), tivirumab (anti-hepatitis B), and urtoxazumab (anti-*E. coli*).

An antibody or antigen-binding fragment of use may be chimeric, humanized or human. The use of chimeric antibodies is preferred to the parent murine antibodies because they possess human antibody constant region sequences and therefore do not elicit as strong a human anti-mouse antibody (HAMA) response as murine antibodies. The use of humanized antibodies is even more preferred, in order to further reduce the possibility of inducing a HAMA reaction. Techniques for humanization of murine antibodies by replacing murine framework and constant region sequences with corresponding human antibody framework and constant region sequences are well known in the art and have been applied to numerous murine anti-cancer antibodies. Antibody humanization may also involve the substitution of one or more human framework amino acid residues with the corresponding residues from the parent murine framework region sequences. As discussed below, techniques for production of human antibodies are also well known.

The therapeutic formulation may comprise an antibody fragment, such as F(ab')$_2$, Fab, scFv, Fv, or a fusion protein utilizing part or all of the light and heavy chains of the F(ab')$_2$, Fab, scFv. The antibody may also be multivalent, or multivalent and multispecific. The antibody may include human constant regions of IgG1, IgG2a, IgG3, or IgG4.

In more preferred embodiments, the allotype of the antibody may be selected to minimize host immunogenic response to the administered antibody, as discussed in more detail below. A preferred allotype is a non-G1m1 allotype (nG1m1), such as G1m3, G1m3,1, G1m3,2 or G1m3,1,2. The non-G1m1 allotype is preferred for decreased antibody immunoreactivity. Surprisingly, repeated subcutaneous administration of concentrated nG1m1 antibody was not found to induce significant immune response, despite the enhanced immunogenicity of subcutaneous administration.

Various embodiments may concern use of the subject methods and compositions to treat a disease, including but not limited to non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas, melanomas, sarcomas, gliomas, and skin cancers. The carcinomas may include carcinomas of the oral cavity, gastrointestinal tract, pulmonary tract, lung, breast, ovary, prostate, uterus, endometrium, cervix, urinary bladder, pancreas, bone, brain, connective tissue, liver, gall bladder, kidney, skin, central nervous system, and testes.

In addition, the subject methods and compositions may be used to treat an autoimmune disease, for example acute immune thrombocytopenia, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, diabetes mellitus (e.g., juvenile diabetes), Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

In alternative embodiments, the concentrated antibody formulation may be of use to treat a metabolic disease, such as type-2 diabetes or amyloidosis, a cardiovascular disease, such as atherosclerosis, or a neurologic disease, such as Alzheimer's disease. Antibodies of use for therapy of such conditions are known in the art, as discussed in more detail below.

In certain embodiments, disease therapy may be enhanced by combination therapy with one or more other therapeutic agents as part of this invention. Known therapeutic agents of use in this invention include immunomodulators (such as cytokines, lymphokines, chemokines, and growth factors, and their inhibitors), sphingosine inhibitors, hormones, hormone antagonists, oligonucleotides (such as siRNA or RNAi), photoactive therapeutic agents, anti-angiogenic agents and pro-apoptotic agents. Other more traditional therapeutic agents, such as cytotoxic drugs or radionuclides, may be administered before, concurrently with, or after the concentrated antibody.

BRIEF DESCRIPTION OF THE DRAWINGS

The following drawings are provided to illustrate preferred embodiments of the invention. However, the claimed subject matter is in no way limited by the illustrative embodiments disclosed in the drawings.

FIG. 7. Comparison of veltuzumab (SEQ ID NO:33) vs. rituximab (SEQ ID NO:34) heavy chain constant region sequences. Identical residues are indicated by asterisks. The two different allotype antibodies differ in heavy chain constant region sequence by only four amino acid residues. The light chain constant region sequences are identical between the two antibodies.

FIG. 8. The amino acid sequences of hL243. The entire variable and constant region sequence of hL243 IgG4P heavy chain is shown as SEQ ID NO:37, with the constant region underlined. The constant region sequence alone of hL243 IgG4P heavy chain is shown as SEQ ID NO:38. The entire variable and constant region sequence of the hL243 light chain is shown as SEQ ID NO:39, with the constant region underlined. The constant region sequence alone of hL243 light chain is shown as SEQ ID NO:40.

DETAILED DESCRIPTION

Definitions

Figure 1:
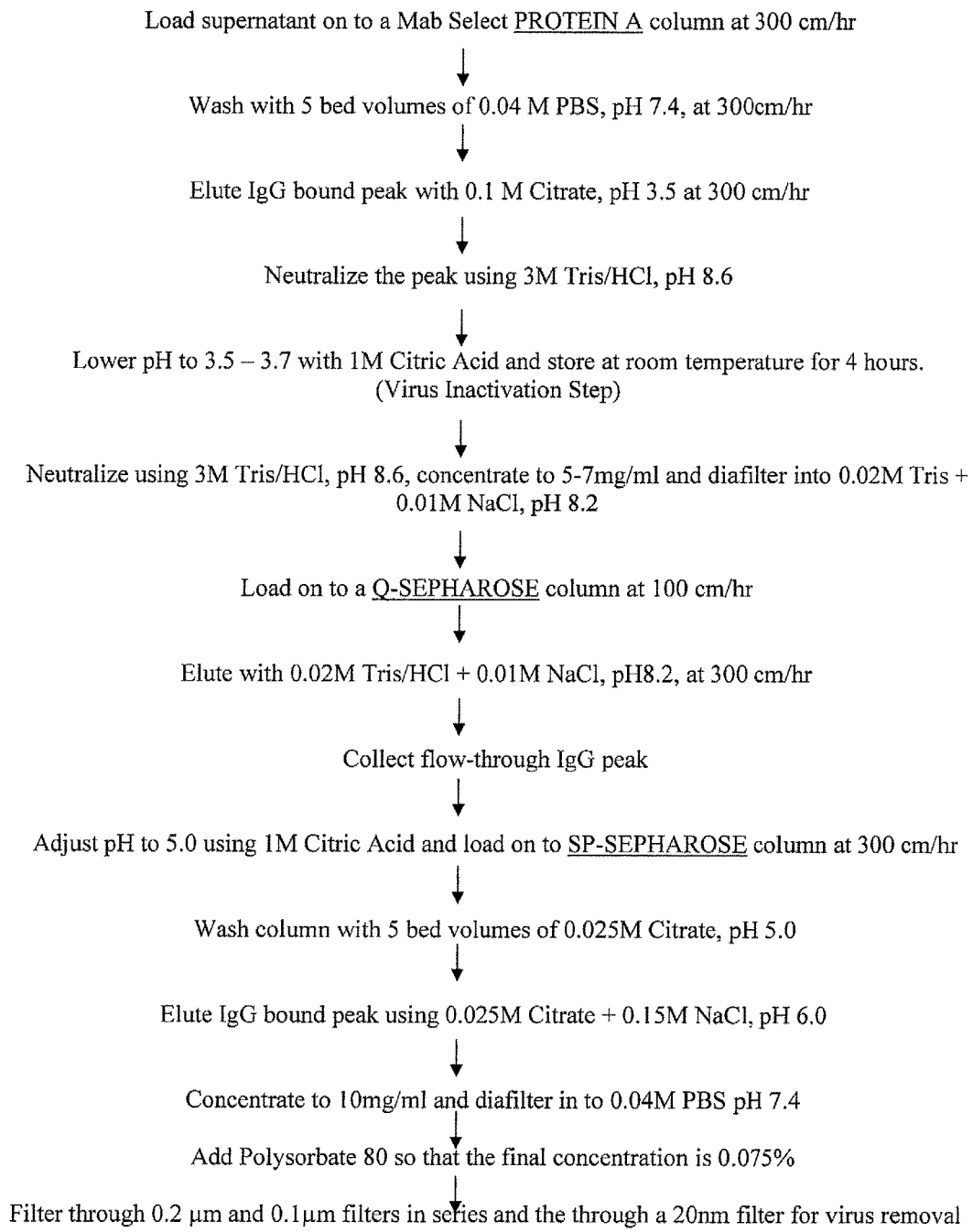
FIG. 1. Exemplary protocol for column chromatography purification of antibody from cell culture medium.

The following definitions are provided to facilitate understanding of the disclosure herein. Where a term is not specifically defined, it is used in accordance with its plain and ordinary meaning.

As used herein, the terms "a", "an" and "the" may refer to either the singular or plural, unless the context otherwise makes clear that only the singular is meant.

An "antibody" refers to a full-length (i.e., naturally occurring or formed by normal immunoglobulin gene fragment recombinatorial processes) immunoglobulin molecule (e.g., an IgG antibody) or an immunologically active (i.e., antigen-binding) portion of an immunoglobulin molecule, like an antibody fragment.

An "antibody fragment" is a portion of an antibody such as F(ab')$_2$, F(ab)$_2$, Fab', Fab, Fv, scFv, single domain antibodies (DABs or VHHs) and the like, including half-molecules of IgG4 (van der Neut Kolfschoten et al., 2007, Science 317:1554-1557). Regardless of structure, an antibody fragment binds with the same antigen that is recognized by the intact antibody. For example, an anti-CD74 antibody fragment binds with an epitope of CD74. The term "antibody fragment" also includes isolated fragments consisting of the variable regions, such as the "Fv" fragments consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region.

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody.

A "human antibody" is an antibody obtained from transgenic mice that have been genetically engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229,275).

A "therapeutic agent" is an atom, molecule, or compound that is useful in the treatment of a disease. Examples of therapeutic agents include but are not limited to antibodies, antibody fragments, drugs, cytokine or chemokine inhibitors, proapoptotic agents, tyrosine kinase inhibitors, toxins, enzymes, nucleases, hormones, immunomodulators, antisense oligonucleotides, siRNA, RNAi, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds.

An "immunoconjugate" is a conjugate of an antibody with an atom, molecule, or a higher-ordered structure (e.g., with a liposome), a therapeutic agent, or a diagnostic agent. A "naked antibody" is an antibody that is not conjugated to any other agent.

A "naked antibody" is generally an entire antibody that is not conjugated to a therapeutic agent. This is so because the Fc portion of the antibody molecule provides effector functions, such as complement fixation and ADCC (antibody dependent cell cytotoxicity) that set mechanisms into action that may result in cell lysis. However, it is possible that the Fc portion is not required for therapeutic function, with other mechanisms, such as apoptosis, coming into play. Naked antibodies include both polyclonal and monoclonal antibodies, as well as certain recombinant antibodies, such as chimeric, humanized or human antibodies.

As used herein, the term "antibody fusion protein" is a recombinantly produced antigen-binding molecule in which an antibody or antibody fragment is linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity.

A "bispecific antibody" is an antibody that can bind simultaneously to two targets which are of different structure. Bispecific antibodies (bsAb) and bispecific antibody fragments (bsFab) may have at least one arm that specifically binds to, for example, a B cell, T cell, myeloid-, plasma-, and mast-cell antigen or epitope and at least one other arm that specifically binds to a targetable conjugate that bears a therapeutic or diagnostic agent. A variety of bispecific antibodies can be produced using molecular engineering.

Preparation of Monoclonal Antibodies

The compositions, formulations and methods described herein may include monoclonal antibodies. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)). General techniques for cloning murine immunoglobulin variable domains have been disclosed, for example, by the publication of Orlandi et al., Proc. Nat'l Acad. Sci. USA 86: 3833 (1989).

Chimeric Antibodies

A chimeric antibody is a recombinant protein that contains the variable domains including the CDRs derived from one species of animal, such as a rodent antibody, while the remainder of the antibody molecule; i.e., the constant domains, is derived from a human antibody. Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and $IgG_1$ constant region domains. This publication also provides the nucleotide sequences of the LL2 light and heavy chain variable regions, $V_k$ and $V_H$, respectively.

Humanized Antibodies

A chimeric monoclonal antibody can be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)). Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

Human Antibodies

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, *Comb. Chem. High Throughput Screen.* 8:117-26; Brekke and Loset, 2003, *Curr. Opin. Pharmacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1st edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized antibody can then be designed and constructed as described by Leung et al. (Mol. Immunol., 32: 1413 (1995)).

cDNA can be prepared from any known hybridoma line or transfected cell line producing a murine antibody by general molecular cloning techniques (Sambrook et al., Molecular Cloning, A laboratory manual, 2nd Ed (1989)). The Vκ sequence for the antibody may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human antibody. Alternatively, the Vκ and $V_H$ expression cassettes can be excised and subcloned into a single expression vector, such as pdHL2, as described by Gillies et al. (*J. Immunol. Methods* 125:191 (1989) and also shown in Losman et al., *Cancer,* 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown in FIG. 7 for the exemplary antibodies rituximab (SEQ ID NO:34) and veltuzumab (SEQ ID NO:33).

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1 m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1 and FIG. 7, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113: 1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

|  | Complete allotype | Heavy chain position and associated allotypes | | | | |
|---|---|---|---|---|---|---|
|  |  | 214 (allotype) | | 356/358 (allotype) | | 431 (allotype) |
| Rituximab | G1m17,1 | K | 17 | D/L | 1 | A — |
| Veltuzumab | G1m3 | R | 3 | E/M | — | A — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Known Antibodies

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056, 509; 7,049,060; 7,045,132; 7,041,803; 7,041,802; 7,041, 293; 7,038,018; 7,037,498; 7,012,133; 7,001,598; 6,998, 468; 6,994,976; 6,994,852; 6,989,241; 6,974,863; 6,965, 018; 6,964,854; 6,962,981; 6,962,813; 6,956,107; 6,951, 924; 6,949,244; 6,946,129; 6,943,020; 6,939,547; 6,921, 645; 6,921,645; 6,921,533; 6,919,433; 6,919,078; 6,916, 475; 6,905,681; 6,899,879; 6,893,625; 6,887,468; 6,887, 466; 6,884,594; 6,881,405; 6,878,812; 6,875,580; 6,872, 568; 6,867,006; 6,864,062; 6,861,511; 6,861,227; 6,861, 226; 6,838,282; 6,835,549; 6,835,370; 6,824,780; 6,824, 778; 6,812,206; 6,793,924; 6,783,758; 6,770,450; 6,767, 711; 6,764,688; 6,764,681; 6,764,679; 6,743,898; 6,733, 981; 6,730,307; 6,720,155; 6,716,966; 6,709,653; 6,693, 176; 6,692,908; 6,689,607; 6,689,362; 6,689,355; 6,682, 737; 6,682,736; 6,682,734; 6,673,344; 6,653,104; 6,652, 852; 6,635,482; 6,630,144; 6,610,833; 6,610,294; 6,605, 441; 6,605,279; 6,596,852; 6,592,868; 6,576,745; 6,572, 856; 6,566,076; 6,562,618; 6,545,130; 6,544,749; 6,534, 058; 6,528,625; 6,528,269; 6,521,227; 6,518,404; 6,511, 665; 6,491,915; 6,488,930; 6,482,598; 6,482,408; 6,479, 247; 6,468,531; 6,468,529; 6,465,173; 6,461,823; 6,458, 356; 6,455,044; 6,455,040; 6,451,310; 6,444,206; 6,441, 143; 6,432,404; 6,432,402; 6,419,928; 6,413,726; 6,406, 694; 6,403,770; 6,403,091; 6,395,276; 6,395,274; 6,387, 350; 6,383,759; 6,383,484; 6,376,654; 6,372,215; 6,359, 126; 6,355,481; 6,355,444; 6,355,245; 6,355,244; 6,346, 246; 6,344,198; 6,340,571; 6,340,459; 6,331,175; 6,306, 393; 6,254,868; 6,187,287; 6,183,744; 6,129,914; 6,120, 767; 6,096,289; 6,077,499; 5,922,302; 5,874,540; 5,814, 440; 5,798,229; 5,789,554; 5,776,456; 5,736,119; 5,716, 595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Particular antibodies that may be of use for therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); rituximab (anti-CD20); tositumomab (anti-CD20); GA101 (anti-CD20); and trastuzumab (anti-ErbB2). Such antibodies are known in the art (e.g., U.S. Pat. Nos. 5,686,072; 5,874, 540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Type-1 and Type-2 diabetes may be treated using known antibodies against B-cell antigens, such as CD22 (epratuzumab), CD74 (milatuzumab), CD19 (hA19), CD20 (veltuzumab) or HLA-DR (hL243) (see, e.g., Winer et al., 2011, Nature Med 17:610-18). Anti-CD3 antibodies also have been proposed for therapy of type 1 diabetes (Cernea et al., 2010, Diabetes Metab Rev 26:602-05).

The pharmaceutical composition of the present invention may be used to treat a subject having a metabolic disease, such amyloidosis, or a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition.

In a preferred embodiment, diseases that may be treated using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541, 440, the Examples section of each incorporated herein by reference) Anti-macrophage, anti-low-density lipoprotein (LDL), anti-MIF (e.g., U.S. Pat. Nos. 6,645,493; 7,517,523, the Examples section of each incorporated herein by reference), and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Antibodies against oxidized LDL induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7Ell, W8E7, NKP15 and GO22 (Becton Dickinson); NEN9.4 (New England Nuclear); and FMCll (Sera Labs). A description of antibodies against fibrin and platelet antigens is contained in Knight, Semin. Nucl. Med., 20:52-67 (1990).

Other antibodies that may be used include antibodies against infectious disease agents, such as bacteria, viruses, mycoplasms or other pathogens. Many antibodies against such infectious agents are known in the art and any such known antibody may be used in the claimed methods and compositions. For example, antibodies against the gp120 glycoprotein antigen of human immunodeficiency virus I (HIV-1) are known, and certain of such antibodies can have an immunoprotective role in humans. See, e.g., Rossi et al., Proc. Natl. Acad. Sci. USA. 86:8055-8058, 1990. Known anti-HIV antibodies include the anti-envelope antibody described by Johansson et al. (AIDS. 2006 Oct. 3; 20(15): 1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agents Chemother. 2006; 50(5):1773-9, all incorporated herein by reference. Antibodies against hepatitis virus are also known and may be utilized (e.g., Dagan and Eren, Curr Opin Mol Ther, 2003, 5:148-55; Keck et al., 2008, Curr Top Microbiol Immunol 317:1-38; El-Awady et al., 2006, 12:2530-35).

Antibodies against malaria parasites can be directed against the sporozoite, merozoite, schizont and gametocyte stages. Monoclonal antibodies have been generated against sporozoites (cirumsporozoite antigen), and have been shown to neutralize sporozoites in vitro and in rodents (N. Yoshida et al., Science 207:71-73, 1980). Several groups have developed antibodies to *T. gondii*, the protozoan parasite involved in toxoplasmosis (Kasper et al., J. Immunol. 129:1694-1699, 1982; Id., 30:2407-2412, 1983). Antibodies have been developed against schistosomular surface antigens and have been found to act against schistosomulae in vivo or in vitro (Simpson et al., Parasitology, 83:163-177, 1981; Smith et al., Parasitology, 84:83-91, 1982: Gryzch et al., J. Immunol., 129:2739-2743, 1982; Zodda et al., J. Immunol. 129:2326-2328, 1982; Dissous et al., J. immunol., 129:2232-2234, 1982)

*Trypanosoma cruzi* is the causative agent of Chagas' disease, and is transmitted by blood-sucking reduviid insects. An antibody has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639-640, 1982).

Anti-fungal antibodies are known in the art, such as anti-Sclerotinia antibody (U.S. Pat. No. 7,910,702); antiglucuronoxylomannan antibody (Zhong and Priofski, 1998, Clin Diag Lab Immunol 5:58-64); anti-*Candida* antibodies (Matthews and Burnie, 2001, 2:472-76); and anti-glycosphingolipid antibodies (Toledo et al., 2010, BMC Microbiol 10:47).

Suitable antibodies have been developed against most of the microorganism (bacteria, viruses, protozoa, fungi, other parasites) responsible for the majority of infections in humans, and many have been used previously for in vitro diagnostic purposes. These antibodies, and newer antibodies that can be generated by conventional methods, are appropriate for use in the present invention.

Antibody Fragments

Antibody fragments which recognize specific epitopes can be generated by known techniques. The antibody fragments are antigen binding portions of an antibody, such as F(ab)$_2$, Fab', Fab, Fv, scFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797; Hwang and Foote, 2005, Methods 36:3-10; Clark, 2000, Immunol Today 21:397-402; J Immunol 1976 117:1056-60; Ellison et al., 1982, Nucl Acids Res 13:4071-79; Stickler et al., 2011, Genes and Immunity 12:213-21).

Multispecific and Multivalent Antibodies

Methods for producing bispecific antibodies include engineered recombinant antibodies which have additional cysteine residues so that they crosslink more strongly than the more common immunoglobulin isotypes. (See, e.g., FitzGerald et al, Protein Eng. 10(10):1221-1225, (1997)). Another approach is to engineer recombinant fusion proteins linking two or more different single-chain antibody or antibody fragment segments with the needed dual specificities. (See, e.g., Coloma et al., Nature Biotech. 15:159-163, (1997)). A variety of bispecific antibodies can be produced using molecular engineering. In one form, the bispecific antibody may consist of, for example, an scFv with a single binding site for one antigen and a Fab fragment with a single binding site for a second antigen. In another form, the bispecific antibody may consist of, for example, an IgG with two binding sites for one antigen and two scFv with two binding sites for a second antigen. In alternative embodiments, multispecific and/or multivalent antibodies may be produced using the dock-and-lock (DNL) technique as described below.

In certain embodiments, the bispecific antibody may bind to two different antigens, such as antigens selected from the group consisting of CD19, CD20, CD22, CD74, CD79a, CD40L, ILGF-R1, TROP2, CEACAM5, CECAM6, HLA-DR, IFNα, IL-6 and TNF-α. In other embodiments, of use in pretargeting methods described in more detail below, the bispecific antibody may contain at least one binding site for a disease associated antigen, such as a tumor-associated antigen (TAA) and at least one binding site for a hapten on a targetable construct.

Dock-and-Lock (DNL)

In preferred embodiments, bispecific or multispecific antibodies or other constructs may be produced using the dock-and-lock technology (see, e.g., U.S. Pat. Nos. 7,550,143; 7,521,056; 7,534,866; 7,527,787; 7,666,400; 7,858,070; 7,871,622; 7,906,121; 7,906,118 and 7,901,680, the Examples section of each incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four types of PKA regulatory subunit are RIα, RIβ, RIIα and RIIβ. The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIα, RIβ, RIIα or RIIβ and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chimura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521,056; 7,534,866; 7,527,787; 7,666,400; 7,858,070; 7,871,622; 7,906,121; 7,906,118 and 7,901,680.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256, 395; Stickney et al., Cancer Res. 51:6650, 1991; Yuan et al., Cancer Res. 51:3119, 1991; U.S. Pat. Nos. 6,077,499; 7,011, 812; 7,300,644; 7,074,405; 6,962,702; 7,387,772; 7,052, 872; 7,138,103; 6,090,381; 6,472,511; 6,962,702; and 6,962, 702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-NH$_2$ (SEQ ID NO:41), wherein DOTA is 1,4,7,10-tetraazacyclododecane1,4,7,10-tetraacetic acid and HSG is the histamine succinyl glycyl group. Alternatively, DOTA may be replaced by NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties. Chelating moieties may be used, for example, to bind to a therapeutic and or diagnostic radionuclide, paramagnetic ion or contrast agent.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Preparation of Immunoconjugates

In preferred embodiments, a therapeutic or diagnostic agent may be covalently attached to an antibody or antibody fragment to form an immunoconjugate. Where the immunoconjugate is to be administered in concentrated form by subcutaneous, intramuscular or transdermal delivery, the skilled artisan will realize that only non-cytotoxic agents may be conjugated to the antibody. Where a second antibody or fragment thereof is administered by a different route, such as intravenously, either before, simultaneously with or after the subcutaneous, intramuscular or transdermal delivery, then the type of diagnostic or therapeutic agent that may be conjugated to the second antibody or fragment thereof is not so limited, and may comprise any diagnostic or therapeutic agent known in the art, including cytotoxic agents.

In some embodiments, a diagnostic and/or therapeutic agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetyl-mannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or Vκ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

Therapeutic and Diagnostic Agents

In certain embodiments, the antibodies or fragments thereof may be used in combination with one or more therapeutic and/or diagnostic agents. Where the agent is attached to an antibody or fragment thereof to be administered by subcutaneous, intramuscular or transdermal administration of a concentrated antibody formulation, then only non-cytotoxic agents are contemplated. Non-cytotoxic agents may include, without limitation, immunomodulators, cytokines (and their inhibitors), chemokines (and their inhibitors), tyrosine kinase inhibitors, growth factors, hormones and certain enzymes (i.e., those that do not induce local necrosis), or their inhibitors. Where the agent is co-administered either before, simultaneously with or after the subcutaneous, intramuscular or transdermal antibody formulation, then cytotoxic agents may be utilized. An agent may be administered as an immunoconjugate with a second antibody or fragment thereof, or may be administered as a free agent. The following discussion applies to both cytotoxic and non-cytotoxic agents.

Therapeutic agents may be selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a tyrosine kinase inhibitor, a sphingosine inhibitor, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents, and combinations thereof.

Exemplary drugs may include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Immunomodulators may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, kit-ligand or FLT-3, angiostatin, thrombospondin, endostatin, tumor necrosis factor and LT.

Chemokines of use include RANTES, MCAF, MIP1-alpha, MIP1-Beta and IP-10.

Radioactive isotopes include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{255}$Ac, $^{76}$Br, $^{169}$Yb, and the like.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-placenta growth factor (PlGF) peptides and antibodies, anti-vascular growth factor antibodies (such as anti-VEGF and anti-PlGF), anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

The therapeutic agent may comprise an oligonucleotide, such as a siRNA. The skilled artisan will realize that any siRNA or interference RNA species may be attached to an antibody or fragment thereof for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576, 196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635, 771); IGF-1R (U.S. Pat. No. 7,638,621); ICAM1 (U.S. Pat. No. 7,642,349); complement factor B (U.S. Pat. No. 7,696, 344); p53 (7,781,575), and apolipoprotein B (7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Exemplary siRNA species known in the art are listed in Table 2. Although siRNA is delivered as a double-stranded molecule, for simplicity only the sense strand sequences are shown in Table 2.

TABLE 2

Exemplary siRNA Sequences

| Target | Sequence | SEQ ID NO |
|---|---|---|
| VEGF R2 | AATGCGGCGGTGGTGACAGTA | SEQ ID NO: 1 |
| VEGF R2 | AAGCTCAGCACACAGAAAGAC | SEQ ID NO: 2 |
| CXCR4 | UAAAAUCUUCCUGCCCACCdTdT | SEQ ID NO: 3 |
| CXCR4 | GGAAGCUGUUGGCUGAAAAdTdT | SEQ ID NO: 4 |
| PPARC1 | AAGACCAGCCUCUUUGCCCAG | SEQ ID NO: 5 |
| Dynamin 2 | GGACCAGGCAGAAAACGAG | SEQ ID NO: 6 |
| Catenin | CUAUCAGGAUGACGCGG | SEQ ID NO: 7 |
| E1 A binding protein | UGACACAGGCAGGCUUGACUU | SEQ ID NO: 8 |
| Plasminogen activator | GGTGAAGAAGGGCGTCCAA | SEQ ID NO: 9 |
| K-ras | GATCCGTTGGAGCTGTTGGCGTAGTTCAA GAGACTCGCCAACAGCTCCAACTTTTGGA AA | SEQ ID NO: 10 |
| Sortilin 1 | AGGTGGTGTTAACAGCAGAG | SEQ ID NO: 11 |
| Apolipoprotein E | AAGGTGGAGCAAGCGGTGGAG | SEQ ID NO: 12 |
| Apolipoprotein E | AAGGAGTTGAAGGCCGACAAA | SEQ ID NO: 13 |
| Bcl-X | UAUGGAGCUGCAGAGGAUGdTdT | SEQ ID NO: 14 |
| Raf-1 | TTTGAATATCTGTGCTGAGAACACAGTTC TCAGCACAGATATTCTTTTT | SEQ ID NO: 15 |
| Heat shock transcription factor 2 | AATGAGAAAAGCAAAAGGTGCCCTGTCTC | SEQ ID NO: 16 |
| IGFBP3 | AAUCAUCAUCAAGAAAGGGCA | SEQ ID NO: 17 |
| Thioredoxin | AUGACUGUCAGGAUGUUGCdTdT | SEQ ID NO: 18 |
| CD44 | GAACGAAUCCUGAAGACAUCU | SEQ ID NO: 19 |
| MMP14 | AAGCCTGGCTACAGCAATATGCCTGTCTC | SEQ ID NO: 20 |
| MAPKAPK2 | UGACCAUCACCGAGUUUAUdTdT | SEQ ID NO: 21 |
| FGFR1 | AAGTCGGACGCAACAGAGAAA | SEQ ID NO: 22 |
| ERBB2 | CUACCUUUCUACGGACGUGdTdT | SEQ ID NO: 23 |
| BCL2L1 | CTGCCTAAGGCGGATTTGAAT | SEQ ID NO: 24 |
| ABL1 | TTAUUCCUUCUUCGGGAAGUC | SEQ ID NO: 25 |
| CEACAM1 | AACCTTCTGGAACCCGCCCAC | SEQ ID NO: 26 |
| CD9 | GAGCATCTTCGAGCAAGAA | SEQ ID NO: 27 |
| CD151 | CATGTGGCACCGTTTGCCT | SEQ ID NO: 28 |
| Caspase 8 | AACTACCAGAAAGGTATACCT | SEQ ID NO: 29 |
| BRCA1 | UCACAGUGUCCUUUAUGUAdTdT | SEQ ID NO: 30 |
| p53 | GCAUGAACCGGAGGCCCAUUU | SEQ ID NO: 31 |
| CEACAM6 | CCGGACAGTTCCATGTATA | SEQ ID NO: 32 |

The skilled artisan will realize that Table 2 represents a very small sampling of the total number of siRNA species known in the art, and that any such known siRNA may be utilized in the claimed methods and compositions.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}$F, $^{52}$Fe, $^{110}$In, $^{111}$In, $^{177}$Lu, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Administration

The subject antibodies and immunoglobulins in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active ingredients (i.e., the labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection, more preferably by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising antibodies can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The formulation thereof should be in a solution having a suitable pharmaceutically acceptable buffer such as phosphate, TRIS (hydroxymethyl) aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

The dosage of an administered antibody for humans will vary depending upon such factors as the patient's age, weight, height, sex, general medical condition and previous medical history. Typically, it is desirable to provide the recipient with a dosage of antibody that is in the range of from about 1 mg to 600 mg as a single infusion, although a lower or higher dosage also may be administered. Typically, it is desirable to provide the recipient with a dosage that is in the range of from about 50 mg per square meter ($m^2$) of body surface area or 70 to 85 mg of the antibody for the typical adult, although a lower or higher dosage also may be administered. Examples of dosages of antibodies that may be administered to a human subject are 1 to 1,000 mg, more preferably 1 to 70 mg, most preferably 1 to 20 mg, although higher or lower doses may be used. Dosages may be repeated as needed, for example, once per week for 4-10 weeks, preferably once per week for 8 weeks, and more preferably, once per week for 4 weeks. It may also be given less frequently, such as every other week for several months.

More recently, subcutaneous administration of veltuzumab has been given to NHL patients in 4 doses of 80, 160 or 320 mg, repeated every two weeks (Negrea et al., 2011, Haematologica 96:567-73). Only occasional, mild to moderate and transient injection reactions were observed, with no other safety issues (Id.). The objective response rate (CR+CRu+PR) was 47%, with a CR/CRu (complete response) rate of 24% (Id.). Interestingly, the 80 mg dosage group showed the highest percentage of objective response (⅔, 67%), with one of three patients showing a complete response (Id.). Four out of eight objective responses continued for 60 weeks (Id.). All serum samples evaluated for HAHA were negative (Id.). Although the low sample population reported in this study precludes any definitive conclusions on optimal dosing, it is apparent that therapeutic response was observed at the lowest dosage tested (80 mg).

In certain alternative embodiments, the antibody may be administered by transdermal delivery. Different methods of transdermal delivery are known in the art, such as by transdermal patches or by microneedle devices, and any such known method may be utilized. In an exemplary embodiment, transdermal delivery may utilize a delivery device such as the 3M hollow Microstructured Transdermal System (hMTS) for antibody based therapeutics. The hMTS device comprises a 1 $cm^2$ microneedle array consisting of 18 hollow microneedles that are 950 microns in length, which penetrate approximately 600-700 microns into the dermal layer of the skin where there is a high density of lymphatic channels. A spring-loaded device forces the antibody composition from a fluid reservoir through the microneedles for delivery to the subject. Only transient erythema and edema at the injection site are observed (Burton et al., 2011, Pharm Res 28:31-40). The hMTS device is not perceived as a needle injector, resulting in improved patient compliance.

In alternative embodiments, transdermal delivery of peptides and proteins may be achieved by (1) coadminstering with a synthetic peptide comprising the amino acid sequence of ACSSSPSKHCG (SEQ ID NO:42) as reported by Chen et al. (Nat Biotechnol 2006; 24: 455-460) and Carmichael et al. (Pain 2010; 149:316-324); (2) coadministering with arginine-rich intracellular delivery peptides as reported by Wang et al. (BBRC 2006; 346: 758-767); (3) coadminstering with either AT1002 (FCIGRLCG, SEQ ID NO:43) or Tat (GRKKRRNRRRCG, SEQ ID NO:44) as reported by Uchida et al. (Chem Pharm Bull 2011; 59:196); or (4) using an adhesive transdermal patch as reported by Jurynczyk et al (Ann Neurol 2010; 68:593-601). In addition, transdermal delivery of negatively charged drugs may be facilitated by combining with the positively charged, pore-forming magainin peptide as reported by Kim et al. (Int J Pharm 2008; 362:20-28).

In preferred embodiments where the antibody is administered subcutaneously, intramuscularly or transdermally in a concentrated formulation, the volume of administration is preferably limited to 3 ml or less, more preferably 2 ml or less, more preferably 1 ml or less. The use of concentrated antibody formulations allowing low volume subcutaneous, intramuscular or transdermal administration is preferred to the use of more dilute antibody formulations that require specialized devices and ingredients (e.g., hyaluronidase) for subcutaneous administration of larger volumes of fluid, such as 10 ml or more. The subcutaneous, intramuscular or transdermal delivery may be administered as a single administration to one skin site or alternatively may be repeated one or more times, or even given to more than one skin site in one therapeutic dosing session. However, the more concentrated the formulation, the lower the volume injected and the fewer injections will be needed for each therapeutic dosing.

Methods of Use

In preferred embodiments, the concentrated antibodies are of use for therapy of cancer. Examples of cancers include, but are not limited to, carcinoma, lymphoma, glioma, melanoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, neuroblastoma, cervical cancer, ovarian cancer, liver cancer, bladder cancer, hepatoma, breast cancer, colon cancer, rectal cancer, endometrial cancer or uterine carcinoma, salivary gland carcinoma, kidney or renal cancer, prostate cancer, vulval cancer, thyroid cancer, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to detect or treat malignant or premalignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected and/or treated include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

The exemplary conditions listed above that may be treated are not limiting. The skilled artisan will be aware that antibodies or antibody fragments are known for a wide variety of conditions, such as autoimmune disease, graft-versus-host-disease, organ transplant rejection, cardiovascular disease, neurodegenerative disease, metabolic disease, cancer, infectious disease and hyperproliferative disease.

Exemplary autoimmune diseases include acute idiopathic thrombocytopenic purpura, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, juvenile diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

Infectious diseases may be caused by a variety of pathogenic organisms, such as bacteria, viruses or mycoplasma. Exemplary known infectious agents include, but are not limited to, *Streptococcus agalactiae, Legionella pneumophilia, Streptococcus pyogenes, Esherichia coli, Neisseria gonorrhoeae, Neisseria meningitidis, Pneumococcus, Hemophilus influenzae B, Treponema pallidum*, Lyme disease spirochetes, *Pseudomonas aeruginosa, Mycobacterium leprae, Brucella abortus, Mycobacterium tuberculosis*, HIV-1, HIV-2, HIV-3, Hepatitis A, Hepatitis B, Hepatitis C, Hepatitis D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Vesicular stomatitis virus, Sindbis virus, Lymphocytic choriomeningitis virus, Wart virus, Blue tongue virus, Sendai virus, Reo virus, Polio virus, Dengue virus, Rubella virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumonia*.

Kits

Various embodiments may concern kits containing components suitable for treating diseased tissue in a patient. Exemplary kits may contain at least one concentrated antibody or fragment thereof as described herein. A device capable of delivering the kit components by injection, for example, a syringe for subcutaneous injection, may be included. Where transdermal administration is used, a delivery device such as hollow microneedle delivery device may be included in the kit. Exemplary transdermal delivery devices are known in the art, such as 3M's hollow Microstructured Transdermal System (hMTS), and any such known device may be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Alternatively, the concentrated antibody may be delivered and stored as a liquid formulation. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1. Purification of hLL2 Anti-CD22 Antibody

The hLL2 anti-CD22 antibody (epratuzumab) was designed, constructed, cloned and transfected into myeloma host cells as described in U.S. Pat. Nos. 5,789,554 and 6,187,287, the Examples section of each of which is incorporated herein by reference. Use of appropriate leader sequences results in secretion of the antibody into the serum-free cell culture medium. Cells may be removed by centrifugation and the antibody purified from culture medium as shown, for example, in FIG. 1.

Generally, the purification process for hLL2 IgG and other antibodies described in the following Examples features chromatography on three sequential columns of Protein A, Q-SEPHAROSE® and SP-SEPHAROSE®. Although SEPHAROSE® is used as an exemplary column chromatography resin, the skilled artisan will realize that alternative methods of chromatography and alternative chromatography resins are known in the art and may be used. Further, the anion and cation exchange steps are not limited to Q-SEPHAROSE® and SP-SEPHAROSE®, but may also utilize other anion- and cation-exchange resins known in the art. The last step of the process utilizes a DV20 virus removal filtration, after which the product is tested for sterility.

The Protein A affinity resin used for the first column, MAB SELECT™ (GE Healthcare, Piscataway, N.J.) has a binding capacity of 25-30 mg/mL. The resin was packed up to a 20 cm height in a 40 cm diameter column to a packed bed volume of 25 L, with a maximum loading capacity of 625 gm. Before the antibody containing culture medium was loaded, the packed column was sanitized with 0.1 M acetic acid in 20% ethanol and then re-generated with 0.04 M PBS, pH 7.4. After equilibration, the supernatant was loaded at a maximum flow rate of 300 cm/hr. The column was washed with 0.04 M PBS, pH 7.4, until the absorbance returned to baseline, followed by washing with another 5 bed volumes of 0.04 M PBS, pH 7.4 at 300 cm/hr.

The bound IgG was eluted with 0.1 M citrate, pH 3.5, at a maximum flow rate of 300 cm/hr. The elution profile was monitored by absorbance at 280 nm, using a flow through spectrophotometer. The collected product peak was neutralized to pH 7.0-8.0 using 3 M Tris/HCl, pH 8.6. As an additional virus removal step, the neutralized product peak was titrated to pH 3.5-3.7 using 1 M citric acid. This mixture was incubated at room temperature for four hours and at the end of the incubation, it was neutralized to pH 7.0-8.0 using 3 M Tris/HCl, pH 8.6.

The mixture was then concentrated to 5-7 mg/mL and diafiltered into 0.02 M Tris/HCl, 0.01M NaCl, pH 8.2, in preparation for the next purification step. The diafiltered Protein A purified hLL2 IgG was filtered through a 0.2 µm filter and stored at 2-8° C. until further purification.

The anion exchange resin used for the next column was Q-SEPHAROSE® fast flow resin (GE Healthcare, Piscataway, N.J.). The resin was packed up to a 20 cm height in a 40 cm diameter column, to a packed bed volume of 25 L with a maximum loading capacity of 625 gm. Before the Protein A purified IgG was loaded, the packed column was sanitized with 1 M sodium hydroxide and then regenerated with 0.02 M Tris/HCl, 1.0 M NaCl, pH 8.0. The resin was then equilibrated using 0.02 M Tris/HCl, 0.01M NaCl, pH 8.2. The diafiltered Protein A purified IgG was loaded at a flow rate of 100 cm/hr and the flow through peak was eluted with 0.02 M Tris/HCl, 0.01M NaCl, pH 8.2 at a maximum flow rate of 300 cm/hr. The contaminants eluted from the Protein A column bound to the Q-SEPHAROSE® resin. The Q-SEPHAROSE® purified IgG was filtered using a 0.2-µm filter and stored at 2-8° C. until further purification. Before loading onto the final column, the IgG was titrated to pH 5.0 using 1 M citric acid.

The cation exchange resin used for the last column was SP-SEPHAROSE® fast flow resin (GE Healthcare, Piscataway, N.J.). The resin was packed up to a 20 cm height in a 40 cm diameter column, with a maximum loading capacity of 625 gm. Before the Q-SEPHAROSE® purified hLL2 IgG was loaded, the packed column was sanitized with 1 M sodium hydroxide and then equilibrated with 0.025 M citrate, pH 5.0. The IgG was loaded at a maximum flow rate of 300 cm/hr and the column was washed with 5 bed volumes of 0.025 M citrate, pH 5.0, at 300 cm/hr. The bound IgG peak was then eluted with 0.025 M citrate, 0.15 M sodium chloride, pH 6.0, at a maximum flow rate of 300 cm/hr. The elution profile was monitored by absorbance at 280 nm.

The purified hLL2 IgG was filtered using a 0.2 µm filter and stored at 2-8° C. before $DV_{20}$ filtration. The IgG was concentrated to 9.5-10.5 mg/mL and then diafiltered into 0.04 M PBS, 0.075% Polysorbate 80, pH 7.4. The IgG was then filtered through a 0.2 µm filter into a sterile container, then filtered through a 0.1 µm filter into a sterile pressure vessel, then filtered through a 20 nm filter for virus removal.

Example 2. Purification of hLL1 Anti-CD74 Antibody

The hLL1 anti-CD74 antibody (milatuzumab) was designed, constructed, cloned and transfected into myeloma host cells as described in U.S. Pat. Nos. 7,312,318; 7,772,373; 7,919,087 and 7,931,903, the Examples section of each of which is incorporated herein by reference.

The hLL1 antibody was purified by essentially the same protocol described in Example 1 above, with the following differences. The Protein A resin was packed to a 20 cm height in a 20 cm diameter column, providing a packed bed volume of 6.3 L. The maximum loading capacity of the Protein A column was 220 gm. The Q-SEPHAROSE® column was packed to a 20 cm height in a 30 cm diameter column to a packed bed volume of 14.1 L, with a maximum loading capacity of 300 gm. The SP-SEPHAROSE® column was packed to a 20 cm height in a 20 cm diameter column, with a packed bed volume of 6.3 L and a maximum loading capacity of 220 gm. The purified hLL1 IgG was concentrated to 10-11 mg/mL for $DV_{20}$ filtration. After filtration, 75 mL of 0.04 M PBS, 1% Polysorbate 80, pH 7.4 was added to every liter of purified IgG and the mixture was filtered again through a 0.2 µm filter before storage at 2°-8° C.

Example 3. Purification of hL243 Anti-HLA-DR Antibody

The hL243 anti-HLA-DR antibody was designed, constructed, cloned and transfected into myeloma host cells as described in U.S. Pat. No. 7,612,180, the Examples section of which is incorporated herein by reference.

The hL243 antibody (IMMU-114) was purified by essentially the same protocol described in Example 1 above, with the following differences. The Protein A resin was packed to a 20 cm height in a 20 cm diameter column, providing a packed bed volume of 6.3 L. The maximum loading capacity of the Protein A column was 220 gm. The Protein A purified IgG was concentrated to 5-7 mg/ml and diafiltered into 0.02 M Tris/HCl, 0.05 M NaCl, pH 7.5, before filtration and loading onto the Q-SEPHAROSE® column.

The Q-SEPHAROSE® column was packed to a 20 cm height in a 30 cm diameter column to a packed bed volume of 14.1 L, with a maximum loading capacity of 300 gm. After sanitization with 1 M sodium hydroxide, the resin was equilibrated with 0.02 M Tris/HCl, 0.05 M NaCl, pH 7.5. The flow through peak was eluted with 0.02 M Tris/HCl, 0.05 M NaCl, pH 7.5. The SP-SEPHAROSE® column was packed to a 20 cm height in a 20 cm diameter column, with a packed bed volume of 6.3 L and a maximum loading capacity of 220 gm. After loading and washing, the IgG was eluted with 0.025 M citrate, 0.15 M NaCl, pH 6.0.

The purified hL243 IgG was concentrated to 10-11 mg/mL and diafiltered into 0.04 M PBS, pH 7.4, then filtered through 0.2 and 0.1 µm filters before $DV_{20}$ filtration. After filtration, 75 mL of 0.04 M PBS, 1% Polysorbate 80, pH 7.4 was added to every liter of purified IgG and the mixture was filtered again through a 0.2 µm filter before storage at 2°-8° C.

Example 4. Isotypes of hL243 Anti-HLA-DR Antibody

The hL243 anti-HLA-DR antibody was prepared as described in Example 3 above. An expression vector hL243pdHL2 was constructed by sequentially subcloning the XbaI-BamHI and XhoI/NotI fragments of hL243$V_K$ and $V_H$, respectively, into pdHL2 as described previously (Losman et al., 1997. Cancer, 80:2660). The expression vector pdHL2, as described by Gilles et al. (1989, J. Immunol. Methods 125:191), contains the genomic sequence of the human γ1 chain, therefore, the hL243 is an IgG1/K isotype.

To construct the expression vector for hL243 of other isotypes, such as IgG4/K, the sequence of the human γ1 chain was replaced with that of the human γ4 chain, which was obtained by PCR amplification. The template used was genomic DNA extracted from the ATCC CRL-11397 cell and the primer pair was as below.

```
SacII
                                     (SEQ ID NO: 35)
CCGCGGTCACATGGCACCACCTCTCTTGCAGCTTCCACCAAGGGCCC

EagI
                                     (SEQ ID NO: 36)
CCGGCCGTCGCACTCATTTACCCAGAGACAGGG
```

The amplified PCR product was cloned into TOPO® TA sequencing vector (INVITROGEN®) and the sequence was confirmed by DNA sequencing.

A point mutation, Ser241Pro (based on Kabat numbering) was introduced into the hinge region of the γ4 sequence to avoid formation of half-molecules when the IgG4 antibody is expressed in mammalian cell cultures (Schuurman et al., 2001, Mol. Immunol. 38:1). The human γ4 hinge region sequence between PstI and StuI restriction sites (56 bp) was replaced with a synthetic DNA fragment with substitution of the TCA codon for Ser241 to CCG for Pro. The human γ1 sequence in hL243pdHL2 was substituted with the mutated γ4 sequence, resulting in the final expression vector, designated as hL243γ4PpdHL2, for the IgG4 isotype hL243. The IgG4 isotype was used in subsequent experiments on therapeutic efficacy.

The amino acid sequences of the hL243 IgG4P heavy chain and of the hL243 light chain are shown in FIG. 8.

Example 5. Purification of hA20 Anti-CD20 Antibody

The hA20 anti-CD20 antibody (veltuzumab) was designed, constructed, cloned and transfected into myeloma host cells as described in U.S. Pat. Nos. 7,151,164 and 7,435,803, the Examples section of which is incorporated herein by reference.

The hA20 antibody was purified by essentially the same protocol described in Example 1 above, with the following differences. Protein A resin with a maximum loading capacity of 30 mg/mL was packed to a 19-21 cm height in a 20 cm diameter column, providing a packed bed volume of 6.0-6.6 L. The maximum loading capacity of the Protein A column was approximately 180 gm. The Protein A purified IgG was titrated to pH 3.6-3.8 with 1 M citric acid for virus removal.

The Q-SEPHAROSE® column was packed to a height of 19-21 cm in a 30 cm diameter column to a packed bed volume of 13.4-14.9 L, with a maximum loading capacity of 300 gm. After loading, the flow-through peak was eluted with 0.2 M Tris/HCl, 0.01 M NaCl, pH 8.0.

The SP-SEPHAROSE® column was packed to a 19-21 cm height in a 20 cm diameter column, with a packed bed volume of 6.0-6.6 L and a maximum loading capacity of 180 gm. After loading and washing, the IgG was eluted with 0.025 M citrate, 0.15 M NaCl, pH 6.0.

The purified hA20 IgG was concentrated to 10-11 mg/mL and diafiltered into 0.04 M PBS, pH 7.4, then filtered through 0.2 and 0.1 μm filters before $DV_{20}$ filtration. After filtration, 75 mL of 0.04 M PBS, 1% Polysorbate 80, pH 7.4 was added to every liter of purified IgG and the mixture was filtered again through a 0.2 μm filter before storage at 2°-8° C.

Figure 2:
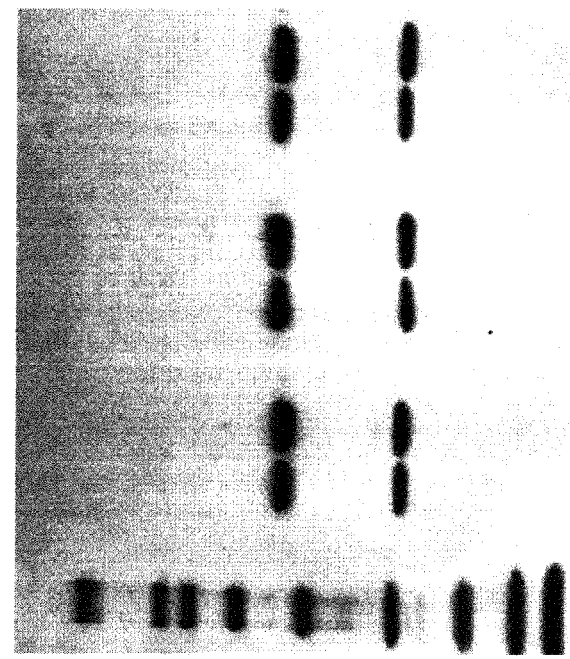
FIG. 2. SDS-polyacrylamide gel electrophoresis of ultrafiltration concentrated antibodies: (A) non-reducing gel, (B) reducing gel. Both gels show (lane 1) MW standards; (lane 2) hLL1 IgG, starting IgG solution (10 mg/mL); (lane 3) concentrated hLL1 IgG, after 2 month storage, (215 mg/mL); (lane 4) hA20 IgG, starting IgG solution (5.1 mg/mL); (lane 5) concentrated hA20 IgG, after 10 month storage, (162 mg/mL); (lane 6) hL243 IgG, starting IgG solution (8.9 mg/mL); (lane 7) concentrated hL243 IgG, after 10 month storage, (101 mg/mL). The MW standards used were respectively 6.5, 14, 21, 31, 45, 66, 97, 116 and 200 KD.
Figure 2:
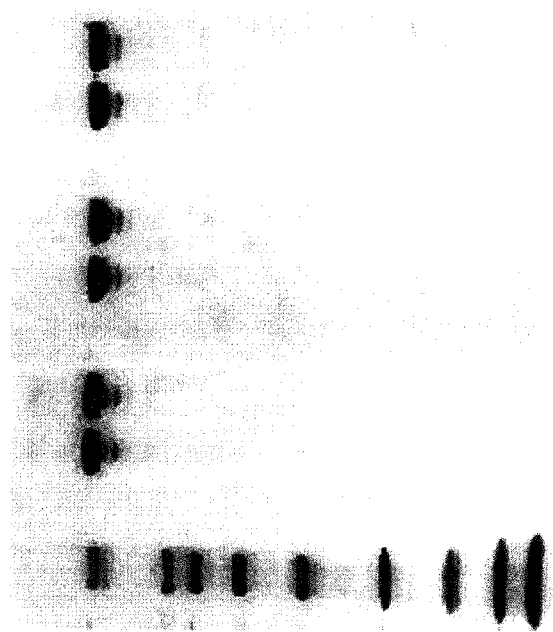
Figure 4:
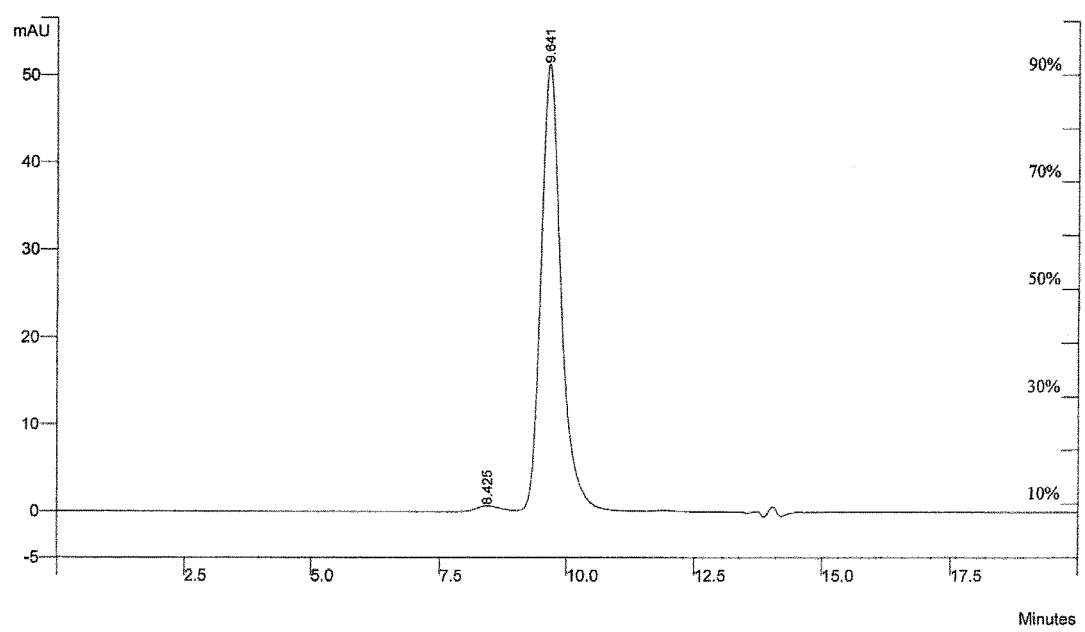
FIG. 4. Representative SE HPLC chromatogram of ultrafiltration concentrated hLL1 IgG solution (215 mg/mL) after 10 months of storage.
Figure 5:
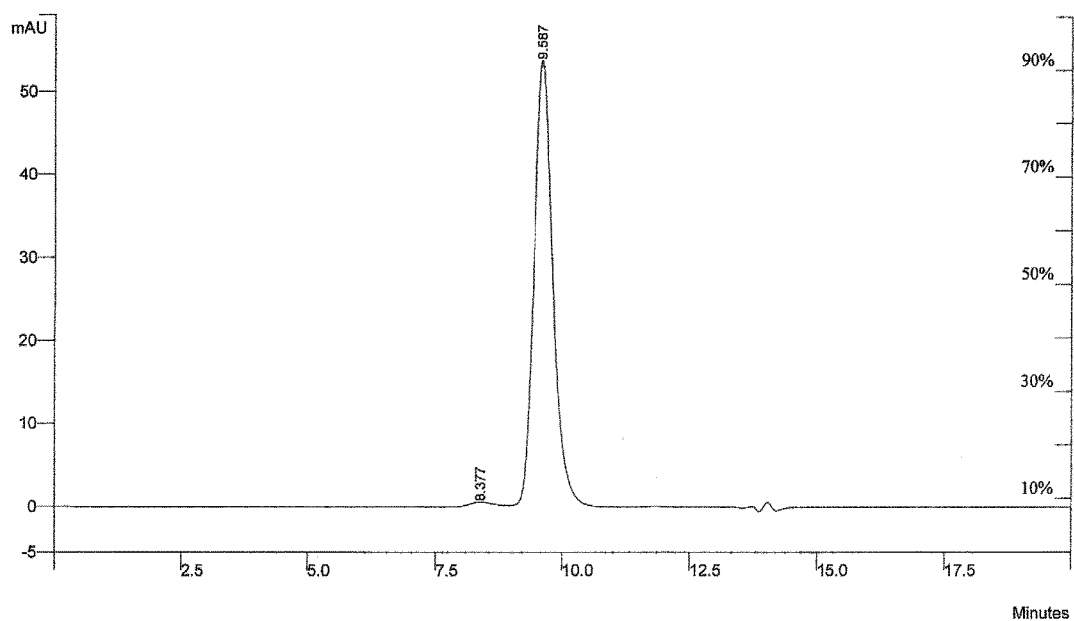
FIG. 5. Representative SE HPLC chromatogram of ultrafiltration concentrated hA20 IgG solution (162 mg/mL) after 10 months of storage.
Figure 6:
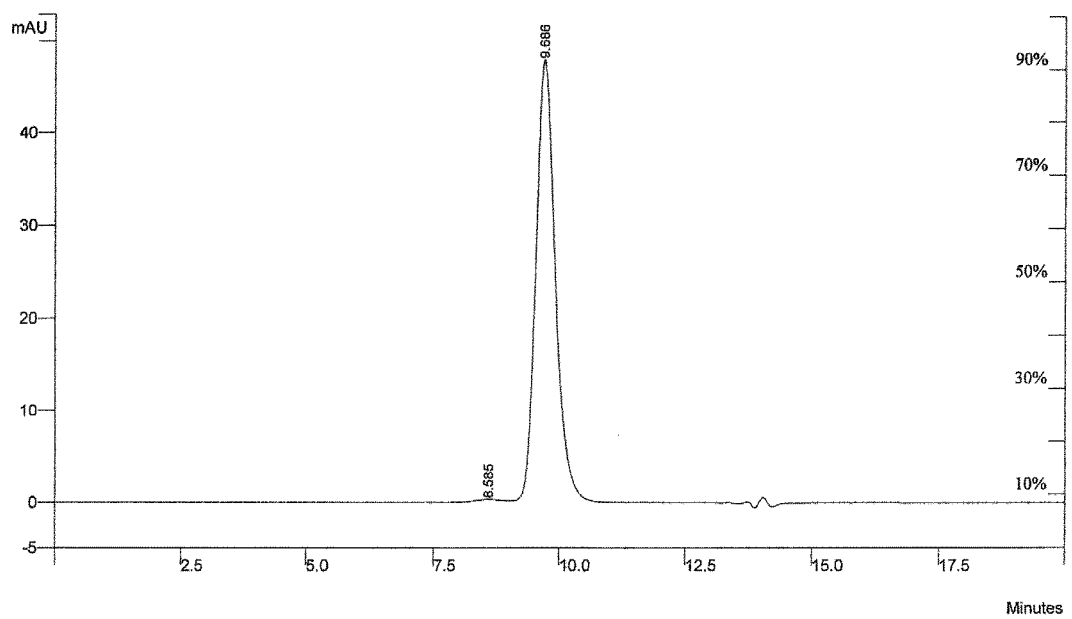
FIG. 6. Representative SE HPLC chromatogram of ultrafiltration concentrated hL243 IgG solution (101 mg/mL) after 10 months of storage.

Example 6. Ultrafiltration Concentration of Humanized Antibodies in High Concentration Formulation Buffer Using ultrafiltration, humanized IgG was concentrated to at least 200 mg/mL in High Concentration Formulation (HCF) buffer, with minimal or no aggregation. A series of analytical assays were performed to monitor any changes during the concentration process. No detectable changes in antibody quality or solution characteristics were observed. The liquid formulation was stable at 2-8° C. for at least 12 months. The stability estimated at 12 months by SE-HPLC (which showed essentially a single peak on the absorbance trace, FIG. 4-6) was between 97 and 99% (Table 4). Reducing and non-reducing PAGE was consistent with the HPLC results (FIG. 2A-2B). The formulation is suitable for subcutaneous injection (SC). Exemplary antibodies tested include milatuzumab (hLL1, anti-CD74), epratuzumab (hLL2, anti-CD22), veltuzumab (hA20, anti-CD20) and hL243 (anti-HLA-DR; IMMU-114).

A High Concentration Formulation (HCF) buffer was developed that was demonstrated to be capable of stabilizing antibody solutions to at least 200 mg/mL concentration (Table 3). In addition to phosphate buffer and NaCl from IV formulation, this SC formulation contains mannitol which has been of use in protein formulations for maintaining stability and isotonicity, and Polysorbate 80 (PS-80) which protects antibodies against aggregation. Since the pI value of most humanized IgG1 antibodies is between 8-9.5, a citric acid/sodium citrate buffer system (buffering range 2.5~5.6) and a low pH (5.2) were used to ensure the protein is in a charged form, and thus more stable in solution.

During ultrafiltration a 50 KD MW cut-off membrane was used, which retained and concentrated the 150 KD IgG molecules while allowing water and small molecules in the formulation buffer to pass through.

The solute concentrations of HCF buffer were 6.2 mM citric acid monohydrate, 105 mM sodium chloride, 1.2 mM sodium citrate dihydrate, 8.7 mM sodium phosphate dibasic, 5.5 mM sodium phosphate monobasic, 66 mM mannitol, pH 5.2, conductivity 11.0-14.0 mS/cm.

An AMICON® Model 8050 Stirred Ultrafiltration Cell (from MILLIPORE®, 50 mL max volume) was used with a 50 KD polyethersulfone filter NMWL (from MILLIPORE®, diameter 44.5 mm) to concentrate the antibodies. Ultra pure argon gas was used to pressurize the system.

The UF-cell with a 50 KD membrane was assembled and connected to the argon gas supply. The cell was rinsed and filled with buffer. With the stirrer on, pressure was applied to run more than two volumes of HCF buffer through the membrane. From this point on, the membrane was maintained in a wet state.

After rinsing of the stirred cell chamber, the residual buffer was discarded and the cell was filled with IgG solution. The stir plate was then started and the pressure applied. The antibody solution was concentrated to approximately one half (½) the original volume, then diafiltered using HCF buffer (5× retentate volume). The process was repeated 3-4 times until the diafiltration was completed and checked to make sure that the pH and conductivity of filtrate was identical to the HCF buffer.

Post-concentration, Polysobate-80 was added so that the final concentration of Polysorbate was 0.1%. The IgG was then filtered through a 0.22-μm filter, placed in clear glass vials, and stored at 2-8° C. until analytical testing was performed.

Each sample was visually inspected against a dark background under light for any particulates and precipitates. IgG protein concentration was measured by UV ($OD_{280}$) absorbance after serial dilutions. SDS-PAGE was performed using pre-cast 4-20% gradient gels. Ten μL of ~1 mg/mL sample was heated at 95° C. for 3 minutes in the presence (reducing gel) or absence (non-reducing gel) of a 3% 2-mercaptoethanol solution. Gels were stained with 0.1% Coomassie Blue. Isoelectric Focusing (IEF) was performed by standard techniques, using pH 6-10.5 gradient gels. Samples were diluted to 2 mg/mL and applied at 5 μL each along with pI markers and reference standard. Gels were stained with Coomassie Blue and scanned for quantification of pI range.

TABLE 3

| | High Concentration Formulation Compositions | | | |
|---|---|---|---|---|
| Component | hLL1 (Milatuzumab, anti-CD74) | hLL2 (Epratuzumab, anti-CD22) | hA20 (Veltuzumab, anti-CD20) | hL243 (anti-HLA-DR) |
| $IgG_1$ | 213 mg/mL | 109 mg/mL | 162 mg/ml | 101 mg/mL |
| $Na_2HPO_4 \cdot 7H_2O$ | 2.30 g | | | |
| $NaH_2PO_4 \cdot H_2O$ | 0.76 g | | | |
| Sodium Chloride | 6.16 g | | | |
| Polysorbate 80 (w/v) | 1.0 mL (polysobate-80 was added at the end of the concentration step) | | | |
| Sodium Citrate Dihydrate | 0.34 g | | | |
| Citric Acid Monohydrate | 1.3 g | | | |
| Mannitol | 12.0 g | | | |
| WFI (qs) | 1 L | | | |
| pH (adjusted by NaOH) | 5.2 | | | |

Size Exclusion HPLC (SE-HPLC) was carried out using a BECKMAN® HPLC system (Model 116), with a BIO-SIL® SEC 250 column. The sample was diluted to about 1 mg/mL and 60 μL was injected. The elution buffer was composed of 0.05 M NaH$_2$PO$_4$, 0.05 M Na$_2$HPO$_4$ and 1 mM EDTA, pH 6.8. The elution was monitored by UV absorbance at 280 nm.

Figure 3:
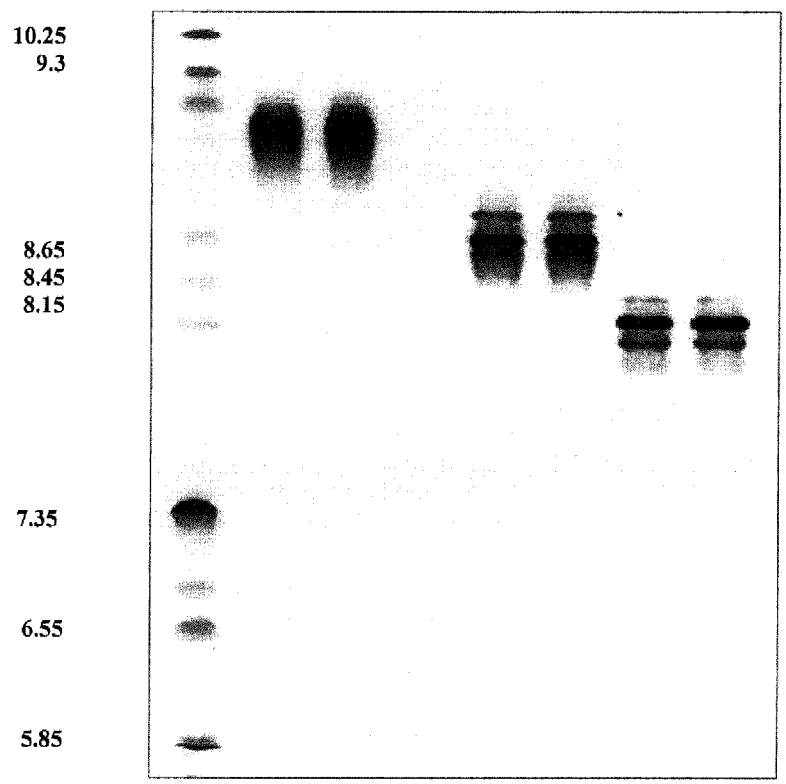
FIG. 3. Isoelectric focusing gel of ultrafiltration concentrated antibodies showing (lane 1) pI standards; (lane 2) hLL1 IgG, starting IgG solution (10 mg/mL); (lane 3) concentrated hLL1 IgG, after 2 month storage, (215 mg/mL); (lane 4) hA20 IgG, starting IgG solution (5.1 mg/mL); (lane 5) concentrated hA20 IgG, after 10 month storage, (162 mg/mL); (lane 6) hL243 IgG, starting IgG solution (8.9 mg/mL); (lane 7) concentrated hL243 IgG, after 10 month storage, (101 mg/mL). The MW standards used were respectively 6.5, 14, 21, 31, 45, 66, 97, 116 and 200 KD.

All analytical results are summarized in Table 4. The SDS-PAGE gel (FIG. 2A non-reducing and FIG. 2B, reducing), IEF gel (FIG. 3), and SE-HPLC chromatograms (FIG. 4 to FIG. 6) are shown. It can be seen that ultrafiltration concentration of the IgG in HCF buffer from 101 mg/mL to 213 mg/mL did not result in any detectable changes in the purified IgG.

TABLE 4

Analytical Results

| | Antibody | | | |
|---|---|---|---|---|
| | hLL1 | hLL2 | hA20 | hL243 |
| | Concentration | | | |
| | 213 mg/mL | 109 mg/mL | 102 mg/mL | 101 mg/mL |
| SE-HPLC (Area Percent) | 98.3% (0 month) 97.5% (4 month) | 98.5% (0 Month) 97.3% (12 Month) | 98.9% (0 Month) 98.5% (12 Month) | 99.3% (0 Month) 98.8% (12 Month) |
| Visual inspection | Clear yellowish color | Clear yellowish color | Clear yellowish color | Clear slight milk color |
| SDS-Page gel | Reducing and Non-Reducing SDS-PAGE gels for all samples of concentrated MAb showed a band pattern similar to reference standard | | | |
| IEF gel | IEF gel patterns for all samples of concentrated MAb showed a band pattern similar to reference standard | | | |

This study demonstrated that in the HCF buffer, IgG could be concentrated by ultrafiltration up to 213 mg/mL without any visible aggregation or precipitation. Other quality aspects of the antibody such as molecular integrity, charge variation and solution pH were also maintained.

Example 7. High-Protein Concentration Antibody Formulations for Subcutaneous or Intramuscular Injection Alternative high concentration formulations for subcutaneous or intramuscular administration may comprise amino acids, such as arginine or glutamine. A comparison of the maximal protein concentration achievable without precipitation was determined for epratuzumab (humanized anti-CD22), using three different formulations comprising the sugar mannitol and/or the amino acids arginine and glutamic acid (Table 5).

Epratuzumab was applied to a 40 mL MABSELECT® (Protein A) affinity chromatography column, which was washed with phosphate-buffered saline and then diH$_2$O, to remove polysorbate-80 from the original bulk material. The antibody was eluted with 80 mL of 0.05 M sodium citrate, pH 3.5. The eluate was neutralized by the addition of 132 mL of 0.1 M NaH$_2$PO$_4$ and formulated into CPREM buffer by the addition of 60 mL of a 1 M L-arginine monohydrochloride/1 M L-glutamic acid (monosodium salt) solution and 39.6 mL of 1 M mannitol, adjusted to pH 5.3 with HCl and diluted to 600 mL with deionized H$_2$O. The final CPREM formulation contained 66 mM mannitol, 100 mM arginine, 100 mM glutamic acid, 144 mM Na, 100 mM Cl, 7.3 mM citrate, 22 mM phosphate, pH 5.3. A protein concentration of 2.56 mg/mL was measured by UV spectrophotometry at 280 nM (OD$_{280}$).

The 600 mL solution was concentrated 120-fold using a stir-cell concentrator with a 50 kDa MWCO membrane. A protein concentration of 238 mg/mL in the 120× concentrate was measured by OD$_{280}$. There was no evident precipitation by visual inspection and an SE-HPLC trace, which was indistinguishable from that of the pre-concentration material, showed no evidence of aggregation (data not shown). The 120-fold concentrate was separated into three aliquots.

An aliquot (0.5 mL) of the 120× concentrate (238 mg/mL) was maintained in the CPREM formulation and further concentrated to 170× (0.35 mL) and measured by OD$_{280}$ at a protein concentration of 298 mg/mL without evident precipitation. SE-HPLC analysis resolved an identical trace to the pre-concentration material with no aggregation (data not shown). Further concentration of the 30% protein solution was not attempted due to high viscosity and limiting volumes.

A second aliquot was diafiltered into CPRE buffer (100 mM arginine, 100 mM glutamic acid, 144 mM Na, 100 mM Cl, 7.3 mM citrate, 22 mM phosphate, pH 5.3.), which is CPREM buffer without mannitol. The CPRE protein solution was concentrated until a precipitate was evident. At this point, concentration was terminated and the solution was filtered. The protein concentration in the filtered concentrate was measured at 99 mg/mL by OD$_{280}$.

The third aliquot was diafiltered into CPM buffer (66 mM mannitol, 144 mM Na, 100 mM Cl, 7.3 mM citrate, 22 mM phosphate, pH 5.3.), which is CPREM without arginine and glutamic acid. The CPM protein solution was concentrated until a precipitate was evident. At this point, concentration was terminated and the solution was filtered. The protein concentration in the filtered concentrate was measured at 137 mg/mL by OD$_{280}$.

These results suggest that addition of arginine and glutamic acid to the HCF buffer of Example 6 increased the maximum concentration of antibody that could be maintained without precipitation, up to at least 300 mg/ml. Further, since maximum concentration of the hLL1 antibody that could be obtained in HCF buffer was no higher than observed with the other tested antibodies, and substantially lower than observed with the hLL1 antibody in HCF buffer (Table 4), it is expected that comparable increases in stable antibody concentration without precipitation may be obtained for other highly concentrated antibodies.

TABLE 5

High-concentration epratuzumab formulations

| Formulation | Arginine (mM) | Glutamic Acid (mM) | Mannitol (mM) | C$_{max}$ (mg/L) |
|---|---|---|---|---|
| CPREM | 100 | 100 | 66 | 298‡ |
| CPRE | 100 | 100 | 0 | 99* |
| CPM | 0 | 0 | 66 | 137* |

Each formulation contained 144 mM Na, 100 mM Cl, 7.3 mM citrate, 22 mM PO$_4$, pH 5.3
C$^{max}$, maximal achievable concentration at the point of protein precipitation‡ or limiting viscosity*

Example 8. Subcutaneous Injection of Low-Dose Veltuzumab in Non-Hodgkin's Lymphoma (NHL)

Veltuzumab was prepared for subcutaneous administration as described in Examples 5 and 6 above. Seventeen patients with previously untreated or relapsed NHL received 4 doses of 80, 160 or 320 mg veltuzumab injected s.c. every two weeks (Negrea et al., 2011, Haematologica 96:567-573). Responses were assessed by CT scans, with other evaluations including adverse event, B-cell blood levels, serum veltuzumab levels and human anti-veltuzumab (HAHA) titers.

Only occasional, mild to moderate transient injection reactions were seen with the s.c. injection and no other safety issues were observed. The s.c. veltuzumab exhibited a slow release pattern over several days, with mean maximum serum concentrations of 19, 25 and 64 µg/mL at dosages of 80, 160 or 320 mg per injection. Transient B-cell depletion was observed at all dosage levels of veltuzumab. The objective response rate (partial responses plus complete responses plus complete responses unconfirmed) was 47% (8/17) with a complete response/complete response unconfirmed rate of 24% (4/17). Four of the eight objective responses continued for 60 weeks or more. Objective responses were observed at all dose levels of s.c. veltuzumab. All serum samples evaluated for human anti-veltuzumab antibody (HAHA) were negative.

It was concluded that subcutaneous injections of low-dose veltuzumab are convenient, well-tolerated and capable of achieving sustained serum levels, B-cell depletion and durable objective responses in indolent non-Hodgkin's lymphoma.

Example 9. Subcutaneous Injection of Low-Dose Veltuzumab in Immune Thrombocytopenic Purpura (ITP)

Eleven adult chronic ITP patients with platelet counts below $30 \times 10^9$ and who had failed at least one standard therapy received 2 doses of 80 or 120 mg veltuzumab administered two weeks apart, either intravenously (n=7) or subcutaneously (n=4). Of the 9 evaluable patients, the overall objective response rate was 67%, with 33% of patients having a complete response. For the subgroup of 6 patients who did not undergo surgical spleen removal prior to the study, the response rate was 100%, regardless of the route of administration and across the two doses tested. More importantly, 50% of the subgroup completely responded to veltuzumab and continued to maintain their platelet levels at 6 weeks, 6 months and 9 months post therapy. For the 3 patients who had undergone splenectomy, none responded to treatment. Both s.c. and i.v. veltuzumab resulted in B-cell depletion. One patient had an infusion reaction to i.v. veltuzumab and discontinued treatment. Two other patients had minor immunogenic responses to i.v. veltuzumab. No other safety issues were observed and no patients receiving s.c. veltuzumab exhibited an immunogenic response.

This study demonstrated the convenience, safety and efficacy of veltuzumab for ITP therapy and the superiority of s.c. veltuzumab for reducing immunogenic response to administration of the antibody.

Example 10. Subcutaneous Injection of Low-Dose Epratuzumab in Chronic Lymphocytic Leukemia (CLL)

Patients with previously untreated or relapsed CLL receive 4 doses of 80, 160 or 320 mg epratuzumab injected s.c. every week or every two weeks. Divided doses can also be administered twice weekly. Only occasional mild to moderate transient injection reactions are seen with the s.c. injection and no other safety issues are observed. The s.c. epratuzumab exhibits a slow release pattern over several days. Transient B-cell depletion is observed at all dosage levels of epratuzumab, but more strikingly at the two highest doses given for at least 4 weeks. Objective responses are observed at all dose levels of s.c. epratuzumab, but with particularly high responses of 30% (mostly partial responses) at the highest dose. All serum samples evaluated for human anti-epratuzumab antibody (HAHA) are negative.

It is concluded that subcutaneous injections of low-dose epratuzumab are convenient, well-tolerated and capable of achieving sustained serum levels, B-cell depletion and durable objective responses in CLL.

Example 11. Subcutaneous Injection of Low-Dose Epratuzumab in Systemic Lupus Erythematosus (SLE)

Epratuzumab is prepared for subcutaneous administration as described in Examples 1 and 5 or 6 above. Epratuzumab is prepared for subcutaneous administration as described in Examples 1 and 5 or 6 above. An open-label, single-center study of 14 patients with moderately active SLE (total British Isles Lupus Assessment Group (BILAG) score 6 to 12) is conducted. Patients receive 400 mg epratuzumab subcutaneously every week for 6 weeks. Evaluations include safety, SLE activity (BILAG), blood levels of B and T-cells and human anti-epratuzumab antibody (HAHA) titers. Total BILAG scores decrease by at least 50% in all 14 patients, with 92% having decreases continuing to at least 18 weeks. Almost all patients (93%) experience improvement in at least one BILAG B- or C-level disease activity at 6, 10 and 18 weeks. Additionally, 3 patients with multiple BILAG B involvement at baseline have completely resolved all B-level disease activities by 18 weeks. Epratuzumab is well tolerated, with no evidence of immunogenicity or significant changes in T cells, immunoglobulins or autoantibody levels. B-cell levels decrease by an average of 35% at 18 weeks and remain depressed for 6 months post-treatment. These results demonstrate the safety and efficacy of subcutaneous epratuzumab for treatment of SLE.

Example 12. Subcutaneous Injection of Milatuzumab in Multiple Myeloma

Milatuzumab is prepared for subcutaneous administration as described in Examples 1 and 6 above. Patients with relapsed multiple myeloma who had failed at least two standard therapies receive 10 doses of 300 mg milatuzumab, injected s.c. at weekly intervals, of the naked antibody. Responses are classified by EBMT criteria, with PK and immunogenicity evaluated by serum milatuzumab levels and human anti-milatuzumab antibody (HAHA) titers, respectively. Only occasional mild to moderate transient injection-site reactions are seen with the s.c. injection and no other safety issues are observed. The s.c. milatuzumab exhibits a slow release pattern over several days. Objective responses are observed at this dose level of s.c. milatuzumab, as measured by decrease of serum light chains, IgM, circulating and marrow myeloma cells, and improvement in the patient's platelet, hemoglobin, and WBC levels due to improved bone marrow function. All serum samples evaluated for human anti-milatuzumab antibody (HAHA) are negative.

Combination therapy of s.c. naked milatuzumab with bortezomib, doxorubicin or dexamethasone is observed to improve response in multiple myeloma patients, as shown in preclinical models (Stein et al., 2009, Clin Cancer Res 15:2808-17). The combination therapy of milatuzumab with bortezomib, doxorubicin or dexamethasone produces a therapeutic effect that is greater than that observed with milatuzumab alone, drug alone, or the combined effect of antibody or drug administered alone. The combination results in a significant reduction in the optimal doses required of the drugs.

It is concluded that subcutaneous injections of milatuzumab are convenient, well-tolerated and capable of achieving sustained serum levels and durable objective responses in multiple myeloma.

Example 13. Allotype Conversion from G1m1 to nG1m1 Lowers Immunogenicity of IgG1 Therapeutic Antibodies Adalimumab, an anti-TNFα antibody, was constructed from a fully human monoclonal antibody with a G1m17,1 allotype. Adalimumab is approved for therapy of various autoimmune diseases, such as rheumatoid arthritis, psoriatic arthritis, ankylosing spondylitis, Crohn's disease, psoriasis and juvenile idiopathic arthritis. Adalimumab is known to induce an anti-globulin response in some adalimumab-treated patients and antibodies against adalimumab are associated with non-response to treatment (Bartelds et al., 2010, Arthritis Res Ther 12:R221).

Adalimumab is transformed by site-directed mutagenesis from a G1m17,1 allotype to a G1m3 allotype by making the heavy chain substitutions K214R, D356E and L358M, resulting in G1m3-adalimumab.

The native adalimumab and G1m3-adalimumab are administered to patients that are homozygous for G1m17,1, heterozygous for G1m17,1 and G1m3 or homozygous for G1m3. The allotype engineered G1m3-adalimumab is observed to induce a lower rate of immune response in the recipient, with fewer immune reactions that require termination of administration. Surprisingly, the change to G1m3-adalimumab results in a larger reduction in immune response in G1m17,1 homozygotes than in G1m3 homozygotes.

These results demonstrate that changing antibody allotype from G1m1 to nG1m1 can result in a reduction in immunogenicity of therapeutic antibodies.

Example 14. Transdermal Administration of Therapeutic Antibodies

A 3M hollow Microstructured Transdermal System (hMTS) is used to deliver a concentrated antibody composition by transdermal administration (Burton et al., 2011, Pharm Res 28:31-40). Up to 1.5 mL of antibody formulation at a concentration of between 100 to 300 mg/mL is administered at a rate of up to 0.25 mL/min. A red blotch, the size of the hMTS array, is observed immediately after patch removal but is faded as to be almost indistinguishable 10 min post-patch removal. Apart from this transient localized reaction, no other adverse infusion-related reaction is observed. Either whole antibodies or antibody fragments are administered. Antibodies administered by transdermal delivery include veltuzumab, milatuzumab, epratuzumab, adalimumab and clivatuzumab. Therapeutic efficacy and $P_K$ profiles are similar to those observed with subcutaneous administration of the same antibodies.

Veltuzumab is prepared for subcutaneous administration as described in Examples 5 and 6 above. Patients with previously untreated or relapsed NHL receive 4 doses of 80, 160 or 320 mg veltuzumab injected transdermally using a 3M hMTS device every two weeks (Negrea et al., 2011, Haematologica 96:567-573; Burton et al., 2011, Pharm Res 28:31-40). Responses are assessed by CT scans, with other evaluations including adverse event, B-cell blood levels, serum veltuzumab levels and human anti-veltuzumab (HAHA) titers.

Only occasional, mild to moderate transient injection reactions were seen with the transdermal injection and no other safety issues were observed. The transdermal veltuzumab exhibits a slow release pattern over several days. Transient B-cell depletion is observed at all dosage levels of veltuzumab. The objective response rate (partial responses plus complete responses plus complete responses unconfirmed) is 45% with a complete response/complete response unconfirmed rate of 25%. Half of the objective responses continue for 60 weeks or more. Objective responses are observed at all dose levels of transdermal veltuzumab. All serum samples evaluated for human anti-veltuzumab antibody (HAHA) are negative.

It is concluded that transdermal administration of low-dose veltuzumab is convenient, well-tolerated and capable of achieving sustained serum levels, B-cell depletion and durable objective responses in indolent non-Hodgkin's lymphoma.

Example 15. Subcutaneous Injection of Bispecific Antibody for Pre-targeting

Anti-TROP2 Bispecific Antibody

TROP2 (also known as epithelial glycoprotein-1 or EGP-1) is a pancarcinoma marker that is expressed at high levels on virtually all prostate carcinomas (PC). The bispecific antibody TF12 (anti-TROP2×anti-HSG) is made by the dock-and-lock technique, as described in Paragraphs 0077-0081 above, using the hRS7 and 679 antibodies. TF12 effectively targets PC, and provides good tumor uptake. The efficacy of pretargeted radioimmunotherapy (PRIT) using TF12 and $^{177}$Lu-labeled diHSG-peptide (IMP288) is studied in mice with s.c. PC3 tumors.

Five groups of athymic mice (n=10) are xenografted with s.c. human PC3 tumors. Mice are injected s.c. with 2.5 nmol of TF12 followed 16 h later by i.v. injection of 0.1 nmol of radiolabeled IMP288. The therapeutic efficacy of one or two cycles (48 h apart) PRIT with TF12/$^{177}$Lu-IMP288 (41 MBq) is compared to that of conventional RIT with $^{177}$Lu-labeled anti-TROP2 mAb at the MTD (11 MBq $^{177}$Lu-hRS7). Control groups receive either PBS or $^{177}$Lu-IMP288 (41 MBq) without pretargeting with TF12.

Mice treated with one cycle of PRIT show improved median survival (121 vs. 82 days). Two cycles of PRIT significantly enhance median survival compared to only one cycle (>160 vs. 121 days, p<0.0001). Therapeutic efficacy of two cycles of PRIT does not differ significantly from RIT with $^{177}$Lu-hRS7 (p=0.067), but mice treated with PRIT show lower hematologic toxicity. Decrease in leukocytes is significantly higher with RIT than observed with PRIT (67% vs. 38%, p=0.028). After 150 days, 70% of the mice treated with two cycles of PRIT and all mice treated with conventional RIT are still alive, compared to none in the control groups.

Pretargeting with TF12 in combination with $^{177}$Lu-IMP288 is an excellent system for specific radioimmunotherapy of prostate cancer. Efficacy is enhanced significantly by adding an extra cycle of PRIT. In view of the limited toxicity there is room for additional treatment cycles or higher doses of $^{177}$Lu-IMP288.

Anti-CD20 Bispecific Antibody

CD20 is a tumor-associated antibody (TAA) that is a significant target for antibody-based therapy in a wide variety of hematologic cancers and autoimmune diseases. The TF4 bispecific antibody comprising hA20 (anti-CD20)× h679 (anti-HSG) was made according to Sharkey et al. (2008, Cancer Res 68:5282-90).

The TF4 bispecific antibody is administered by s.c. injection to nude mice with Ramos B cell lymphomas. Ramos cells ($1\times10^7$) are implanted s.c. in 6- to 8-wk old female BALB/c nude mice 2 to 4 weeks prior to antibody administration. TF4 antibody in amounts ranging from 0.125 to 1.0 nmol are administered, followed at 29 h later by $^{90}$Y-labeled IMP 288 (Sharkey et al., 2008, Cancer Res 68:5282-90). Optimal results are obtained with a 20-fold ration of TF4 to targetable construct peptide.

The TF4 bispecific antibody is cleared rapidly from the blood, with processing in liver, spleen and kidney. At 24 hours, TF4 improves tumor uptake of labeled peptide 2.6 fold and enhances tumor to blood ratio 45-fold compared to an anti-CD20 Fab×anti-HSG Fab chemical conjugate and by 1.6-fold and 1,600-fold, respectively, compared to radiolabeled anti-CD20 IgG. A severe (>90%) and prolonged reduction of WBCs is observed at the maximum dose of $^{90}$Y-labeled anti-CD20 IgG, while pretargeting results in <60% reduction. TF4 pretargeting results in highly significant improvement in survival, curing 33% to 90% of animals even at relatively low doses, whereas most tumors progress rapidly when treated with $^{90}$Y-labeled anti-CD20 IgG.

Example 16. Administration of Bispecific Antibody for Cancer Therapy

Anti-CD20×Anti-CD22 Bispecific Antibody

The CD20 and CD22 antigens are widely expressed in cancers of hematopoietic origin. Combination therapy with anti-CD20 and anti-CD22 antibodies has been demonstrated to be more efficacious than either agent alone and to be effective for therapy of cancers resistant to single agent treatments (e.g., Leonard et al., 2005, J Clin Oncol 23:5044-51; Qu et al., 2008, Blood 111:2211-19; Gupta et al., 2010, Blood 116:3258-67). Using the techniques disclosed herein, therapy with different antibodies may be administered as combinations of the individual antibodies, or as bispecific antibody constructs.

A bispecific construct comprising the anti-CD20 antibody veltuzumab and the anti-CD22 antibody epratuzumab are prepared by the dock-and-lock (DNL) technique as previously described (U.S. Pat. Nos. 7,521,056; 7,527,787; 7,534,866; the Examples section of each of which incorporated herein by reference). Concentrated solutions of bispecific DNL construct of between 100 and 300 mg/ml are prepared as described in Examples 6 and 7 above. The concentrated bispecific DNL construct is administered to patients with recurrent B-cell lymphoma by s.c. injection at dosages ranging from 200 to 600 mg per injection, once a week for four weeks. Patients are selected with indolent histologies (including follicular lymphoma), aggressive NHL and DLBCL.

The treatment is well tolerated with minimal infusion-related transient reactions. Over 60% of patients with follicular NHL achieve objective response (OR), with a over 50% complete responses (CRs). Over 60% of patients with DLBCL achieve OR with 50% CRs. Median time to progression for all indolent NHL patients is 17.8 months.

It is concluded that therapy with an anti-CD22×anti-CD20 bispecific antibody is efficacious for treatment of hematopoietic tumors, with improved efficacy compared to single antibody treatment and decreased toxicity.

Anti-CD20×Anti-CD74 Bispecific Antibody

A bispecific DNL antibody construct comprising veltuzumab (anti-CD20) and milatuzumab (anti-CD74) is prepared as previously described (Gupta et al., 2012, Blood 119:3767-78). A concentrated formulation of the bispecific anti-CD20×anti-CD74 DNL construct is prepared as described in Examples 6 and 7 above and is administered by s.c. injection to subjects with mantle cell lymphoma (MCL) and other lymphomias or leukemias.

The juxtaposition of CD20 and CD74 on MCL cells by the bispecific antibody results in homotypic adhesion and triggers intracellular changes that include loss of mitochondrial transmembrane potential, production of reactive oxygen species, rapid and sustained phosphorylation of ERKs and JNK, down-regulation of pAkt and Bcl-xL and lysosomal membrane permeabilization, resulting in cell death. The bispecific antibody significantly extends the survival of nude mice bearing MCL xenografts in a dose-dependent manner. Other lymphoma and leukemia cell lines are also depleted by exposure to the bispecific antibody. The results demonstrate the in vitro and in vivo efficacy of the anti-CD20×anti-CD74 bispecific antibody construct for therapy of hematopoietic tumors.

All patents and other references cited in the specification are indicative of the level of skill of those skilled in the art to which the invention pertains, and are incorporated herein by reference, including any Tables and Figures, to the same extent as if each reference had been incorporated by reference individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

SEQUENCE LISTING

```
<160> NUMBER OF SEQ ID NOS: 44

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1
aatgcggcgg tggtgacagt a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagctcagca cacagaaaga c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 3
uaaaaucuuc cugcccacct t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 4
ggaagcuguu ggcugaaaat t                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aagaccagcc ucuuugccca g                                              21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 6
ggaccaggca gaaaacgag                                                    19

<210> SEQ ID NO 7
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuaucaggau gacgcgg                                                      17

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugacacaggc aggcuugacu u                                                 21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggtgaagaag ggcgtccaa                                                    19

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatccgttgg agctgttggc gtagttcaag agactcgcca acagctccaa ctttggaaa       60

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aggtggtgtt aacagcagag                                                   20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
```

```
aaggtggagc aagcggtgga g                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaggagttga aggccgacaa a                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 14
uauggagcug cagaggaugt t                                              21

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tttgaatatc tgtgctgaga acacagttct cagcacagat attctttt                 49

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aatgagaaaa gcaaaaggtg ccctgtctc                                      29

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aaucaucauc aagaaagggc a                                              21

<210> SEQ ID NO 18
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 18
augacuguca ggauguugct t                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaacgaaucc ugaagacauc u                                              21

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagcctggct acagcaatat gcctgtctc                                      29

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 21
ugaccaucac cgaguuuaut t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagtcggacg caacagagaa a                                              21

<210> SEQ ID NO 23
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 23
cuaccuuucu acggacgugt t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgcctaagg cggatttgaa t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
ttauuccuuc uucgggaagu c                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaccttctgg aacccgccca c                                              21

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gagcatcttc gagcaagaa                                                 19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 28
catgtggcac cgtttgcct                                                    19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aactaccaga aggtatacc t                                                  21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 30 ucacagoguc cuuuauguat t                                                 21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
gcaugaaccg gaggcccaut t                                                 21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccggacagtt ccatgtata                                                    19

<210> SEQ ID NO 33
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Ser Thr Lys Gly Pro Ser Val Phe Pro Leu Ala Pro Ser Ser Lys
```

```
            1               5                  10                 15
        Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Leu Gly Thr Gln Thr
        65                  70                  75                  80

Tyr Ile Cys Asn Val Asn His Lys Pro Ser Asn Thr Lys Val Asp Lys
                            85                  90                  95

Arg Val Glu Pro Lys Ser Cys Asp Lys Thr His Thr Cys Pro Pro Cys
                        100                 105                 110

Pro Ala Pro Glu Leu Leu Gly Gly Pro Ser Val Phe Leu Phe Pro Pro
                        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
        145                 150                 155                 160

Tyr Val Asp Gly Val Glu Val His Asn Ala Lys Thr Lys Pro Arg Glu
                        165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
        225                 230                 235                 240

Met Thr Lys Asn Gln Val Ser Leu Thr Cys Leu Val Lys Gly Phe Tyr
                        245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                        275                 280                 285

Leu Tyr Ser Lys Leu Thr Val Asp Lys Ser Arg Trp Gln Gln Gly Asn
                        290                 295                 300

Val Phe Ser Cys Ser Val Met His Glu Ala Leu His Asn His Tyr Thr
        305                 310                 315                 320

Gln Lys Ser Leu Ser Leu Ser Pro Gly Lys
                        325                 330

<210> SEQ ID NO 34
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
             35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Ala Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ccgcggtcac atggcaccac ctctcttgca gcttccacca agggccc    47

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 36
ccggccgtcg cactcattta cccagagaca ggg                                    33

<210> SEQ ID NO 37
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37
```

Gln Val Gln Leu Gln Gln Ser Gly Ser Glu Leu Lys Lys Pro Gly Ala
1               5                   10                  15

Ser Val Lys Val Ser Cys Lys Ala Ser Gly Phe Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Arg Glu Pro Thr Tyr Ala Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Asp Ile Thr Ala Val Val Pro Thr Gly Phe Asp Tyr Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu

```
                     340                 345                 350
Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 38
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Arg Gln Lys Pro Gly Lys Ala Pro Lys Leu Leu Val
        35                  40                  45

Phe Ala Ala Ser Asn Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Thr Thr Pro Trp
                85                  90                  95

Ala Phe Gly Gly Gly Thr Lys Leu Gln Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DOTA
<220> FEATURE:
<221> NAME/KEY: MOD_RES
<222> LOCATION: (2)..(2)
<223> OTHER INFORMATION: Lys(HSG)
<220> FEATURE:
<221> NAME/KEY: MOD_RES
<222> LOCATION: (4)..(4)
<223> OTHER INFORMATION: Lys(HSG)
<220> FEATURE:
<223> OTHER INFORMATION: C-term NH2

<400> SEQUENCE: 41

Phe Lys Tyr Lys
1

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Cys Ser Ser Ser Pro Ser Lys His Cys Gly
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Cys Ile Gly Arg Leu Cys Gly
1               5

<210> SEQ ID NO 44
<211> LENGTH: 12
<212> TYPE: PRT

```
<213> ORGANISM: Human immunodeficiency virus

<400> SEQUENCE: 44

Gly Arg Lys Lys Arg Arg Asn Arg Arg Arg Cys Gly
1               5                   10
```

What is claimed is:

1. A method of subcutaneous, intramuscular or transdermal administration of a therapeutic antibody or immunoglobulin comprising:
   a) obtaining a composition comprising the antibody or immunoglobulin at a concentration of at least 225 mg/ml, wherein the composition further comprises citric acid monohydrate, sodium chloride, sodium citrate dihydrate, sodium phosphate dibasic, sodium phosphate monobasic, polysorbate 80 and mannitol at a pH of 4.5 to 5.5 and wherein the antibody is selected from the group consisting of hR1 (anti-IGF-1R), hPAM4 (anti-mucin), hA20 (anti-CD20), hA19 (anti-CD19), hIMMU31 (anti-AFP), hLL1 (anti-CD74), hLL2 (anti-CD22), hMu-9 (anti-CSAp), hL243 (anti-HLA-DR), hL243 IgG4P (anti-HLA-DR), hMN-14 (anti-CEACAM5), hMN-15 (anti-CEACAM6), hRS7 (anti-EGP-1), hMN-3 (anti-CEACAM6), and hRFB4 (anti-CD22); and
   b) administering the composition to a patient by subcutaneous, intramuscular or transdermal delivery, wherein the volume of the composition administered is selected from the group consisting of 3 ml or less, 2 ml or less and 1 ml or less.

2. The method of claim 1, wherein the composition comprises 6.2 mM citric acid monohydrate, 105 mM sodium chloride, 1.2 mM sodium citrate dihydrate, 8.7 mM sodium phosphate dibasic, 5.5 mM sodium phosphate monobasic, 0.1% polysorbate 80 and 66 mM mannitol.

3. The method of claim 1, wherein the antibody or immunoglobulin is concentrated to at least 250 mg/ml or at least 300 mg/ml.

4. The method of claim 1, wherein the amount of antibody or immunoglobulin administered is selected from the group consisting of 40 mg, 80 mg, 160 mg, 240 mg and 320 mg.

5. The method of claim 1, wherein the administration is repeated.

6. The method of claim 1, wherein the subcutaneously, intramuscularly or transdermally administered antibody is effective at a lower dose than the same antibody administered intravenously.

7. The method of claim 1, wherein the pH of the composition is 5.2.

8. The method of claim 1, wherein the composition further comprises arginine and glutamic acid.

9. The method of claim 1, wherein the antibody has glutamate at Kabat residue 356 and methionine at Kabat residue 358 of the antibody heavy chain.

10. The method of claim 9, wherein the antibody has arginine at Kabat residue 214 of the antibody heavy chain.

11. The method of claim 9, wherein the antibody has glutamate at Kabat residue 356, methionine at Kabat residue 358 and alanine at Kabat residue 431 of the antibody heavy chain.

12. The method of claim 9, wherein the antibody has alanine at Kabat residue 153 and valine at Kabat residue 191 of the antibody light chain.

13. The method of claim 9, wherein the antibody comprises heavy chain constant region amino acid residues arginine-214, glutamic acid-356, methionine-358 and alanine-431.

14. The method of claim 1, wherein the antibody is selected from the group consisting of a monoclonal antibody, an antigen-binding fragment of a monoclonal antibody, a bispecific antibody, a multispecific antibody, an immunoconjugate and an antibody fusion protein.

15. The method of claim 1, wherein the immunoconjugate comprises at least one non-cytotoxic therapeutic or diagnostic agent.

16. The method of claim 15, wherein the therapeutic agent is selected from the group consisting of an immunomodulator, a cytokine, a chemokine, a tyrosine kinase inhibitor, a growth factor, a stem cell growth factor, a lymphotoxin, a hematopoietic factor, a colony stimulating factor (CSF), an interleukin (IL), an interferon (IFN), a hormone and an enzyme.

17. The method of claim 15, wherein the therapeutic agent is selected from the group consisting of erythropoietin, thrombopoietin tumor necrosis factor-α (TNF), TNF-β, granulocyte-colony stimulating factor (G-CSF), granulocyte macrophage-colony stimulating factor (GM-CSF), interferon-α, interferon-β, interferon-γ, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1.alpha., IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-23, IL-25, LIF, FLT-3, angiostatin, thrombospondin, endostatin and LT.

18. The method of claim 1, wherein the antibody is a naked antibody.

19. The method of claim 18, further comprising administering at least one therapeutic agent to said individual.

20. The method of claim 19, wherein the therapeutic agent is selected from the group consisting of a drug, a prodrug, a toxin, an enzyme, a tyrosine kinase inhibitor, a sphingosine inhibitor, an immunomodulator, a cytokine, a hormone, a second antibody, a second antibody fragment, an immunoconjugate, a radionuclide, an antisense oligonucleotide, an RNAi, an anti-angiogenic agent, a pro-apoptosis agent and a cytotoxic agent.

21. The method of claim 1, wherein the antibody is selected from the group consisting of epratuzumab, veltuzumab, milatuzumab, hL243 (anti-HLA-DR) and hL243 IgG4P (anti-HLA-DR).

22. The method of claim 1, wherein the antibody is epratuzumab.

23. The method of claim 1, wherein the antibody is veltuzumab.

24. The method of claim 1, wherein the antibody is milatuzumab.

25. The method of claim 1, wherein the antibody is clivatuzumab.

26. The method of claim 1, wherein the antibody is labetuzumab.

27. The method of claim 1, wherein the antibody is hL243.

28. The method of claim 1, wherein the patient has a disease selected from the group consisting of autoimmune disease, immune dysregulation disease, infectious disease, carcinoma, sarcoma, lymphoma, leukemia, chronic lymphocytic leukemia, follicular lymphoma, diffuse large B-cell lymphoma, multiple myeloma, non-Hodgkin's lymphoma, Alzheimer's disease, type-2 diabetes, type-1 diabetes, amyloidosis, cardiovascular disease, neurological disease and metabolic disease.

29. The method of claim 28, wherein the autoimmune disease is selected from the group consisting of acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

30. The method of claim 14, wherein the antibody fragment is selected from the group consisting of $F(ab')_2$, $F(ab)_2$, Fab, Fab' and scFv fragments.

31. The method of claim 14, wherein the bispecific antibody comprises at least one binding site for a tumor-associated antigen and at least one binding site for a hapten and the method further comprises administering to the patient a targetable construct, wherein the targetable construct comprises at least one copy of the hapten and is attached to at least one diagnostic or therapeutic agent.

* * * * *